United States Patent [19]
Desai

[11] Patent Number: 5,556,909
[45] Date of Patent: Sep. 17, 1996

[54] SUBSTITUTED 2-ARYLCARBONYLOXYMETHYL-1,2,5-THIADIAZOLIDIN-3-ONE 1,1-DIOXIDE DERIVATIVES AND COMPOSITIONS AND METHOD OF USE THEREOF

[75] Inventor: Ranjit C. Desai, Harleysville, Pa.

[73] Assignee: Sanofi Winthrop Inc., New York, N.Y.

[21] Appl. No.: 349,341

[22] Filed: Dec. 2, 1994

[51] Int. Cl.$^6$ .......................... C07D 285/10; A61K 31/41
[52] U.S. Cl. ...................... 514/362; 514/210; 514/236.2; 514/299; 514/326; 514/342; 544/134; 546/183; 546/209; 548/135
[58] Field of Search .................... 548/135; 514/362, 514/210, 236.2, 246, 326, 342; 544/134; 546/183, 209

[56] References Cited

U.S. PATENT DOCUMENTS

| | | |
|---|---|---|
| 5,128,339 | 7/1992 | Dunlap et al. . |
| 5,236,917 | 8/1993 | Dunlap et al. . |
| 5,306,818 | 4/1994 | Subramanyam et al. . |

FOREIGN PATENT DOCUMENTS

| | | |
|---|---|---|
| 4141218 | 6/1993 | Germany . |

OTHER PUBLICATIONS

Cha, Biochem. Pharmacol., 1975, 24, 2177–2185.

Groutas et al., Biochemical and Biophysical Research Communications 1994, 198(1), 341–349.

Muller and DuBois, J. Org. Chem. 1989, 54, 4471–4473.

Lee et al., J. Org. Chem. 1989, 54, 3077–3083.

Lee and Kohn, Journal of Pharmaceutical Sciences 1990, 79(8), 716–718.

Hanewacker et al., Arch. Pharm. 1993, 326, 497–498.

Unterhalt and Hanewacker, Arch. Pharm. 1988, 321, 375–376.

Unterhalt and Hanewacker, Arch. Pharm. 1988, 321, 749–751.

Aouf et al., Tetrahedron Letters 1991, 32(45), 6545–6546.

Dewynter et al., Tetrahedron 1993, 49(1), 65–76.

*Primary Examiner*—Robert Gerstl
*Attorney, Agent, or Firm*—Paul E. Dupont; William J. Davis

[57] ABSTRACT

Substituted 2-arylcarbonyloxymethyl-1,2,5-thiadiazolidin-3-one 1,1-dioxide derivatives, pharmaceutical compositions containing them and methods for the treatment of degenerative diseases utilizing them.

20 Claims, No Drawings

SUBSTITUTED 2-ARYLCARBONYLOXYMETHYL-1,2,5-THIADIAZOLIDIN-3-ONE 1,1-DIOXIDE DERIVATIVES AND COMPOSITIONS AND METHOD OF USE THEREOF

BACKGROUND OF THE INVENTION (a) Field of The Invention

The invention relates to substituted 2-arylcarbonyloxymethyl- 1,2,5-thiadiazolidin-3-one 1,1-dioxide derivatives, to pharmaceutical compositions containing the same and to the method of use thereof in the treatment of degenerative diseases.

(b) Information Disclosure Statement

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carboxyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carboxyl side of the bond is typically Ala, Val, Ser, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Cha, Biochem. Pharmacol., 1975, 24, 2177–2185, discusses kinetic approaches to the study of the binding of inhibitors to macromolecules, such as enzymes, and methods for the determination of such parameters as the inhibition constants, reaction rates and bound and unbound enzyme concentrations.

Groutas et al., Biochemical and Biophysical Research Communications 1994, 198(1), 341–349 disclose compounds of the formula:

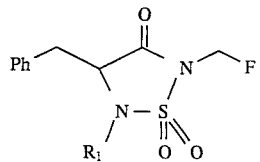

wherein $R_1$ is H, methyl, benzyl, $CH_2COOt$-Bu or $CH_2COOBzl$ and their in vitro inhibitory activity towards human leukocyte elastase.

Muller and DuBois, J. Org. Chem. 1989, 54, 4471–4473 disclose compounds of the formula:

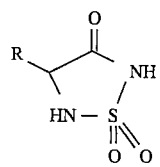

wherein R is H, $CH_3$, benzyl or $(CH_2)_2SCH_3$. The compounds were tested for sweet taste activity and were found to be not sweet or to have sweetness potencies of less than 10 times sucrose.

Lee et al., J. Org. Chem. 1989, 54, 3077–3083 disclose the synthesis of compounds of the formula:

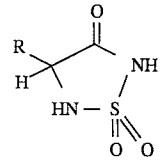

wherein R is phenethyl, phenyl or 1-naphthyl. No utility is disclosed for these compounds.

Lee and Kohn, Journal of Pharmaceutical Sciences 1990, 79(8), 716–718 disclose compounds of the formula:

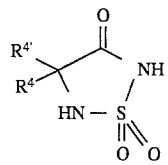

wherein $R^4$ is phenethyl, phenyl or 1-naphthyl and $R^{4'}$ is hydrogen, or $R^4$ and $R^{4'}$ are both phenyl. The compounds were tested for anticonvulsant activity and three of the four compounds were found to be devoid of anticonvulsant activity.

Hanewacker et al., Arch. Pharm. 1993, 326, 497–498 disclose the synthesis of compounds of the formula:

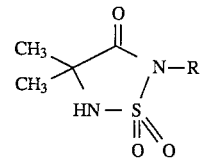

wherein R is $CH_2CH(CH_3)_2$, cyclopropylmethyl, $CH_2Ph$, $(CH_2)_2Ph$, 2-furanylmethyl, 1-naphthylmethyl, or 3-indolylethyl.

Unterhalt and Hanewacker, Arch. Pharm. 1988, 321, 375–376 disclose the synthesis of compounds of the formula:

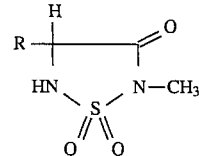

wherein R is hydrogen, methyl, isopropyl, $CH_2CH(CH_3)_2$ or benzyl without an indication of utility.

Unterhalt and Hanewacker, Arch. Pharm. 1988, 321, 749–751 disclose the synthesis of compounds of the formula:

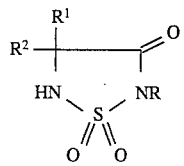

wherein $R=CH_3$, $R^1=H$ and $R^2=$3-indolylmethyl; $R=CH_3$, $R^1=H$, and $R^2=$Phenyl; $R=C_2H_5$, $R^1=H$ and $R^2=$phenyl;

R=isopropyl, $R^1$=H, and $R^2$=phenyl; R=methyl, $R^1$=CH$_3$O(O)CCH$_2$, and $R^2$=H; R=CH$_3$, $R^1$=HO(O)CCH$_2$ and $R^2$=H; R=CH$_3$, $R^1$=C$_2$H$_5$ and $R^2$=phenyl; R=$R^1$=$R^2$=CH$_3$; and R=C$_2$H$_5$, $R^1$=$R^2$=CH$_3$.

Aouf et al., Tetrahedron Letters 1991, 32 (45), 6545–6546 disclose the synthesis of 4-phenylmethyl-1,2,5-thiadiazolidin-3-one 1,1-dioxide.

Dewynter et al., Tetrahedron 1993, 49 (1), 65–76 disclose the synthesis of compounds of the formula:

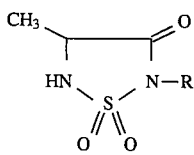

wherein R is CH$_2$Ph or CH$_2$CH(CH$_3$) (C$_2$H$_5$).

Dunlap et al., U.S. Pat. No. 5,236,917, issued Aug. 17, 1993 disclose a series of 2-substituted saccharin derivatives, such as 4-(1-methylethyl)-2-[(3-oxo-1,2,5-thiadiazolidin-2-yl)methyl]-1,2-benzisothiazol-3 (2H)-one S, S, 1,1-tetraoxide, 2-(1-methyl-1H-tetrazol-5-yl-thiomethyl) saccharin and various 2-halomethyl saccharin derivatives, which are stated to be useful in the treatment of degenerative diseases.

Strasser et al., German Patent Application DE 4141218, published Jun. 17, 1993, disclose a series of thiadiazolidin-3-one 1,1-dioxide derivatives as intermediates in the synthesis of various 1,1-dioxo-[1,2,6] thiadiazinecarboxamides which are stated to be potentially useful as analgesics, antipyretics and inflammation inhibitors.

Subramanyam et al., U.S. Pat. No. 5,306,818, issued Apr. 26, 1994, disclose a series of 4-$R^4$-$R^5$-2-saccharinylmethyl aryl carboxylates and 4,5, 6, 7-tetrahydro-2-saccharinylmethyl aryl carboxylates which are stated to be useful in the treatment of degenerative diseases. A similar disclosure is found in Dunlap et al., U.S. Pat. No. 5,128,339, issued Jul. 7, 1992.

SUMMARY OF THE INVENTION

The invention relates to compounds of the Formula I:

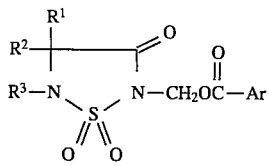

wherein:

Ar is phenyl, or phenyl substituted with from one to three, the same or different, members of the group consisting of lower-alkyl, perfluorolower-alkyl, perchlorolower-alkyl, lower-alkoxy, halogen, hydroxy, and -O-(alkylene)-N=B, wherein N=B is amino, lower-alkylamino, dilower-alkylamino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, or 1-imidazolyl;

$R^1$ is hydrogen, lower-alkyl, phenyl-lower-alkyl, or halolower-alkyl;

$R^2$ is hydrogen, lower-alkyl, phenyl-lower-alkyl, or halolower-alkyl; and $R^3$ is hydrogen, or lower-alkyl; or $R^2$ and $R^3$ together are

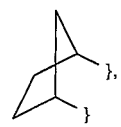

1,3-propylene, 1,4-butylene, or either of 1,3-propylene or 1,4-butylene substituted with one or two lower-alkyl groups; or pharmaceutically acceptable acid-addition salts of basic members thereof; or where applicable, an enantiomer or a racemic mixture thereof.

The compounds of the present invention inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

Preferred compounds of the Formula I above are those wherein Ar is phenyl, or phenyl substituted with from one to three, the same or different, members of the group consisting of lower-alkyl, lower-alkoxy, halogen, hydroxy, and -O-(alkylene)-N=B, wherein N=B is 1-pyrrolidinyl or 4-morpholinyl; and $R^1$ $R^2$ and $R^3$ are as defined directly above; or pharmaceutically acceptable acid-addition salts of basic members thereof; or where applicable, an enantiomer or a racemic mixture thereof.

Particularly preferred compounds of the Formula I above are those wherein Ar is phenyl substituted with from one to three, the same or different, members of the group consisting of halogen, and -O-(alkylene)-N=B, wherein N=B is 1-pyrrolidinyl or 4-morpholinyl; $R^1$ is hydrogen, methyl, propyl, isopropyl, (CH$_2$)$_2$C (Cl) (CH$_3$)$_2$, 3-methylbutyl, or benzyl; $R^2$ is hydrogen, methyl, propyl, isopropyl, (CH$_2$)$_2$C (Cl) (CH$_3$)$_2$, 3-methylbutyl, or benzyl;and $R^3$ is hydrogen, methyl, or ethyl; or $R^2$ and $R^3$ together are

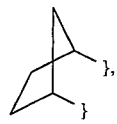

1,3-propylene, 1,4-butylene, or either of 1,3-propylene or 1,4-butylene substituted with one or two lower-alkyl groups; or pharmaceutically acceptable acid-addition salts of basic members thereof; or where applicable, an enantiomer or a racemic mixture thereof.

Preferred species of the Formula I above are 2-(2,6-dichlorophenylcarbonyloxymethyl)-4-propyl-5-methyl-1,2,5-thiadiazolidin-3-one 1,1-dioxide and 2-(2,6-dichlorophenylcarbonyloxymethyl)-4-(3-methylbutyl)-5-methyl-1,2,5-thiadiazolidin-3-one 1,1-dioxide.

The invention further relates to a pharmaceutical composition for the treatment of degenerative diseases which comprises a pharmaceutically acceptable carrier, adjuvant, diluent or vehicle together with an effective proteolytic enzyme inhibiting amount of a compound of the Formula I.

The invention further relates to a method for the treatment of degenerative diseases which comprises administering to a patient in need of such treatment an effective proteolytic enzyme inhibiting amount of a compound of the Formula I.

DETAILED DESCRIPTION INCLUSIVE OF PREFERRED EMBODIMENTS

The term lower-alkyl as used herein means linear or branched hydrocarbon chains having one to about five carbon atoms and thus includes methyl, ethyl, propyl, isopropyl, n-butyl, sec-butyl, 3-methylbutyl; n-pentyl, and the like.

The term halogen, halo, or halide as used herein means chlorine, bromine, iodine, and fluorine.

The term lower-alkoxy as used herein means linear or branched alkyloxy substituents having one to about four carbon atoms and thus includes methoxy, ethoxy, propoxy, isopropoxy, butoxy, sec-butoxy and the like.

The term alkylene as used herein means divalent, saturated radicals, including branched chain radicals, of from two to about five carbon atoms which have their free valences on different carbon atoms and thus includes 1,2-ethylene, 1,3-propylene, 1,4-butylene, 1,5-pentylene, 1-methyl-1,2-ethylene, and the like.

The numbering system used throughout this specification is shown in the ring system which is illustrated below. This ring

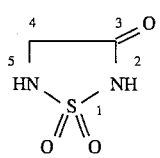

system is named in the chemical literature as a 1,2,5-thiadiazolidin-3-one 1,1-dioxide.

The synthesis of the compounds of the invention may be outlined as shown in Scheme A:

SCHEME A

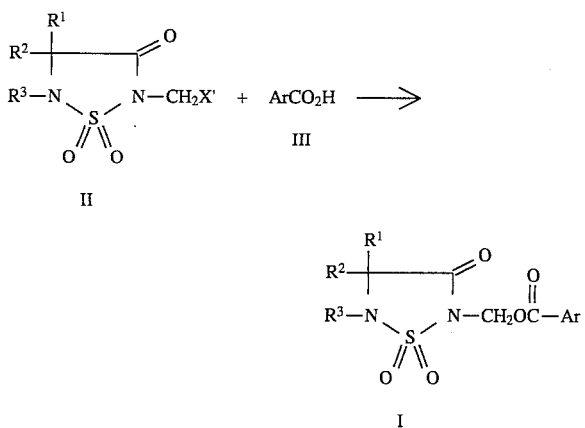

A suitably substituted 2-halomethyl-1,2,5-thiadiazolidin-3-one 1,1-dioxide derivative of the formula II, wherein X' is a halogen, preferably chlorine, in a suitable organic solvent, such as dimethylformamide, or toluene, is treated with an excess of a compound of the formula III, in the presence of an excess of a base, i.e. triethylamine, or potassium carbonate, optionally in the presence of a catalytic amount of a tetraalkylammonium halide, preferably tetrabutylammonium bromide, at a temperature in the range of about room temperature up to the boiling point of the solvent used, to afford the compounds of the formula I.

Alternatively, the compounds of the Formula I can be prepared by reacting a compound of the Formula II with at least one mole of either a) an alkali metal salt of a compound of the Formula III, i.e. the cesium salt, or b) the thallous salt of a compound of the Formula III, in a suitable organic solvent, such as dimethylformamide, optionally in the presence of a catalytic amount of a tetraalkylammonium halide, preferably tetrabutylammonium bromide, at a temperature in the range of about room temperature up to the boiling point of the solvent used.

It will be appreciated that the compounds of the formula I possess an asymmetric carbon at position C-4 of the 1,2,5-thiadiazolidin-3-one 1,1-dioxide ring and are thus capable of existing as enantiomers. Unless otherwise specified herein, the invention is intended to extend to each of the enantiomeric forms including the racemates. In some cases there may be advantages, i.e. greater potency, to using a particular enantiomer when compared to the other enantiomer or the racemate in the treatment of degenerative diseases and such advantages can be readily determined by those skilled in the art. The separate enantiomers may be synthesized from chiral starting materials or the racemates may be resolved by conventional procedures which are well known in the art of chemistry such as chiral chromatography, fractional crystallization of diastereomeric salts and the like.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 2-halomethyl-1,2,5-thiadiazolidin-3-one 1,1-dioxides of the formula II, which are required for the synthesis of the compounds of the formula I, can be prepared as shown in Scheme B:

SCHEME B

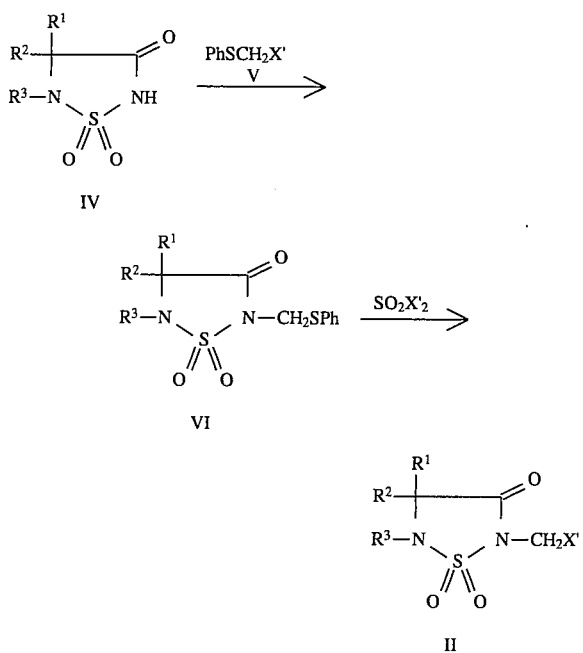

A suitably substituted 1,2,5-thiadiazolidin-3-one 1,1-dioxide of the formula IV, or an ammonium salt thereof, or a cesium salt thereof (prepared by the treatment of a compound of the formula IV in a lower-alkanol solvent, i.e. methanol, with cesium carbonate at a temperature of about room temperature), in a suitable organic solvent, such as toluene, dimethylformamide or a mixture of said solvents, is treated with an excess of a halomethyl phenyl sulfide of the Formula V, wherein X' is a halogen, preferably chlorine, in the presence of a catalytic amount of a tetralower-alkylammonium halide, such as tetrabutylammonium bromide, (note, however, that the use of the tetralower-alkylammonium halide is optional when the cesium salt of the compound of the formula IV is utilized), at a temperature in the range of about room temperature up to the boiling point of the solvent or solvent mixture used, preferably at the boiling point of the solvent or solvent mixture used, to afford the compounds of the formula VI. The compound of the formula VI can then be treated with an excess of a sulfuryl halide of the formula $SO_2X'_2$, wherein X' is a halogen, preferably chlorine, in a suitable organic solvent, such as methylene chloride, at a temperature in the range of about room temperature up to the boiling point of the solvent used, to afford the compounds of the formula II.

Alternatively, the compounds of the Formula II can be prepared directly from the compounds of the Formula IV by treating a compound of the Formula IV, or an alkali metal salt thereof, i.e. the sodium salt, with an excess of paraformaldehyde and an excess of a haloacid in acetic acid, preferably HBr in acetic acid, at a temperature in the range of about room temperature up to the boiling point of the solvent mixture used.

The suitably substituted 1,2,5-thiadiazolidin-3-one 1,1-dioxides of the formula IV can be prepared as shown in Scheme C:

SCHEME C

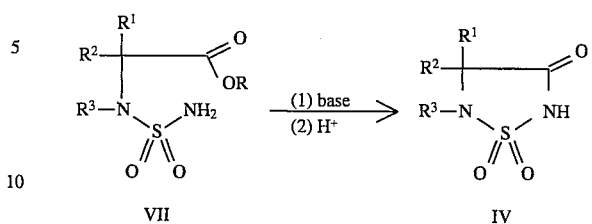

A suitably substituted compound of the formula VII wherein R is lower-alkyl, in an appropriate lower-alkanol solvent, such as methanol, or ethanol, is treated with an excess of an alkali metal lower-alkoxide; i.e. sodium methoxide, or sodium ethoxide, at a temperature in the range of about room temperature up to the boiling point of the solvent used, followed by treatment with a proton source, such as BIO-RAD® 50W-X8 H⁺ ion exchange resin, to afford the compounds of the formula IV.

Alternatively, when the compounds of the formula IV wherein $R^3$ is lower-alkyl are desired, one can proceed as illustrated in Scheme D:

SCHEME D

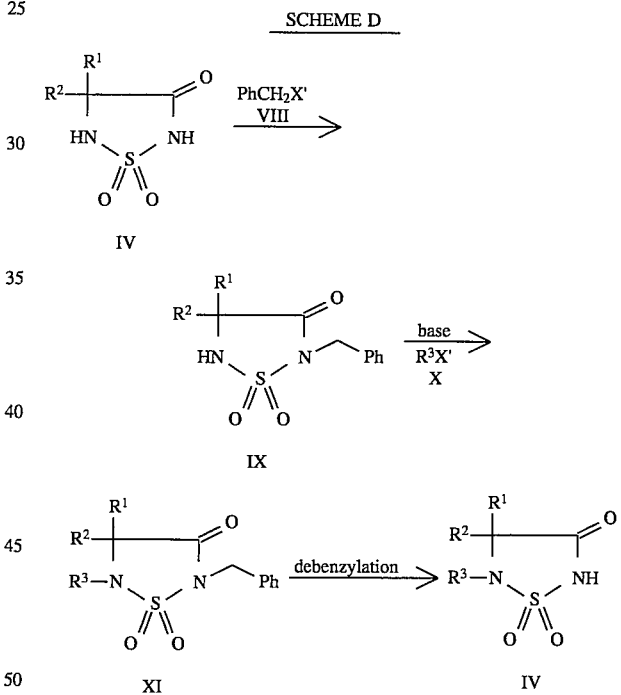

A compound of the formula IV wherein $R^3$ is hydrogen, is treated with an excess of a benzyl halide of the formula VIII, wherein X' is a halogen, preferably bromine, in a suitable organic solvent, i.e. toluene, dimethylformamide, or a mixture thereof, in the presence of a catalytic amount of a tetralower-alkylammonium halide, preferably tetrabutylammonium bromide, at a temperature in the range of about room temperature up to the boiling point of the solvent, or solvent mixture used, to afford the compounds of the formula IX. The compounds of the formula IX can then be treated with an excess of an alkylating agent ($R^3X'$) of the formula X, wherein $R^3$ is lower-alkyl and X' is a halogen, preferably iodine, in a suitable organic solvent, such as tetrahydrofuran, in the presence of at least one mole of a base, such as potassium tertbutoxide, at a temperature in the range of about 0° C. up to the boiling point of the solvent used, preferably at a temperature in the range of about 0° C. up to about room temperature, to afford a compound of the formula XI. The compound of the formula XI can then be debenzylated by treatment with an excess of an appropriate hydrogen donor, preferably ammonium formate, in the presence of an appropriate catalyst, preferably palladium on carbon, in a suitable lower-alkanol solvent, such as methanol, at a temperature in the range of about room temperature up to the boiling point of the solvent used, preferably at a temperature of about room temperature, to afford the compounds of the formula IV wherein $R^3$ is lower-alkyl.

The compounds of the formula VII, which are required for the synthesis of the compounds of the formula IV, can be prepared as illustrated in Scheme E:

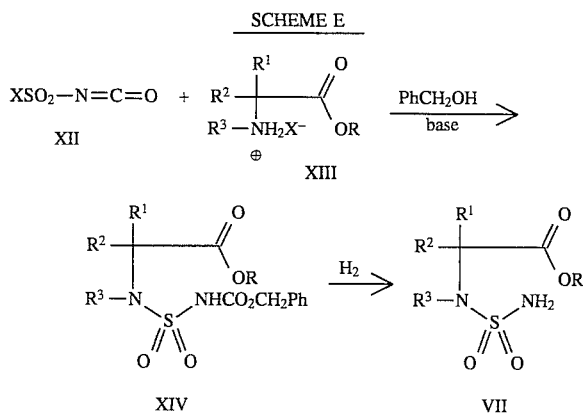

A halosulfonyl isocyanate of the formula XII, wherein X is a halogen, preferably chlorine, is treated with an excess of an α-amino acid ester of the formula XIII, wherein R is lower-alkyl and $X^-$ is a halogen, preferably chlorine, and an excess of benzyl alcohol, in the presence of an excess of a base, such as triethylamine, in an appropriate organic solvent, such as methylene chloride, at a temperature in the range of about −10° C. up to about room temperature, to afford a compound of the formula XIV (Note, if desired, the α-amino acid ester can be used as the limiting reagent rather than the halosulfonyl isocyanate). The compound of the formula XIV can then be hydrogenated at a hydrogen pressure of about 50–60 psi, in a lower-alkanol solvent, such as methanol, or ethanol, in the presence of a catalyst, preferably palladium on carbon, to produce the compounds of the formula VII.

The compounds of the formula III are either commercially available, or they can be prepared by procedures known in the art (see, for example, U.S. Pat. Nos. 5,306,818 and 5,128,339 which are incorporated herein by reference), or by the procedures described hereinbelow in the examples. The halomethyl phenyl sulfides of the formula V, the benzyl halides of the formula VIII, the alkylating agents ($R_3X'$) of the formula X, halosulfonyl isocyanates of the formula XII and the α-amino acid esters of the formula XIII are either commercially available, or they can be prepared by procedures known in the art, or by the procedures described hereinbelow in the examples.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

(a)

To a stirred solution of 7.36 ml (84.9 mmol) of chlorosulfonyl isocyanate in 150 ml of methylene chloride was added phenylmethanol (8.82 ml, 84.7 mmol) at 0°–5° C. After stirring the above solution for 1.5 hours at this temperature, a solution of 15.62 g (93.25 mmol) of 2-aminopentanoic acid methyl ester hydrochloride in 500 ml of methylene chloride containing triethylamine (25.54 g, 0.2528 mol) was added at 0°–5° C., and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride/ethyl acetate (4:1, 2×200 ml) and the combined organic layer was washed with brine, dried, and concentrated in vacuo to yield 28.2 g (87.6%) of 2-(N-carbobenzyloxyaminosulfonyl)aminopentanoic acid methyl ester (Formula XIV: R=$CH_3$; $R^1$=H; $R^2$=propyl; $R^3$=H) as a solid, m.p. 76°–78° C.

(b)

A solution of 2-(N-carbobenzyloxyaminosulfonyl) aminopentanoic acid methyl ester (26.7 g) in methanol (200 ml) under nitrogen was cooled to 0° C. and 1.5 g of 10% Pd/C was added. The mixture was placed into a Parr Apparatus and hydrogenated for 2 hours. The catalyst was removed on a pad of CELITE® and the filtrate was concentrated in vacuo and purified by flash silica gel chromatography (4%–6% methanol in methylene chloride) to afford 11.0 g (62%) of 2-(aminosulfonylamino) pentanoic acid methyl ester (Formula VII: R=$CH_3$; $R^1$=H; $R^2$=propyl; $R^3$=H) as a solid, m.p. 63°–64° C.

(c)

A solution of 2- (aminosulfonylamino) pentanoic acid methyl ester (10.5 g; 0.05 mmol) in methanol (100 ml) was added to a solution of sodium methoxide (3.78 g, from 1.61 g of Na) in 100 ml of methanol and the resulting reaction mixture was refluxed for 18 hours. The mixture was cooled, neutralized with BIO-RAD® 50W-X8 $H^+$ ion exchange resin, and filtered. The filtrate was concentrated in vacuo to yield an oil which was crystallized from methanol/hexane to afford 6.5 g (73%) of 4-propyl-1,2,5-thiadiazolidin-3-one 1,1-dioxide (Formula IV: $R^1$=H; $R^2$=propyl; $R^3$=H).

(d)

To a mixture of 4-propyl-1,2,5-thiadiazolidin-3-one 1,1-dioxide (5.1 g, 28.65 mmol) suspended in 210 ml of toluene was added phenylthiomethyl chloride (4.93 g, 31.49 mmol) and tetrabutylammonium bromide (0.92 g, 2.86 mmol). The resulting mixture was refluxed for 18 hours, cooled, filtered, and the filtrate was concentrated in vacuo. The residue was purified by column chromatography to afford 5.39 g (63%) of 2-phenylthiomethyl- 4-propyl-1,2,5-thiadiazolidin-3-one 1,1-dioxide (Formula VI: $R^1$=H; $R^2$=propyl; $R^3$=H).

(e)

To a solution of 2-phenylthiomethyl-4-propyl-1,2,5-thiadiazolidin- 3-one 1,1-dioxide (5.23 g, 17.43 mmol) in 200 ml of methylene chloride was added sulfuryl chloride (2.15 ml, 26.07 mmol) and the mixture was stirred for 2 hours at room temperature. The mixture was concentrated in vacuo, the residue triturated in hexane (200 ml) for 2 hours, the resulting solid filtered and washed with hexane to afford, after drying, 3.54 g (90%) of 2-chloromethyl- 4-propyl-1, 2,5-thiadiazolidin-3-one 1,1-dioxide (Formula II: $R^1$=H; $R^2$=propyl; $R^3$=H; X'=Cl) as a solid.

(f)

The thallium salt of 2,6-dichlorobenzoic acid (0.96 g; 2.43 mmol, prepared from 0.46 g of 2,6-dichlorobenzoic acid and 0.605 g of $TlOC_2H_5$ in ethanol ) was added to a solution of 2-chloromethyl-4 -propyl-1,2,5-thiadiazolidin-3-one 1,1-dioxide (0.5 g; 2.21 mmol) in DMF (10 ml) containing tetrabutylammonium bromide (70 mg; 0.22 mmol). The mixture was allowed to react at 50° C. for 15 hours and at 100° C. for an additional hour, and then cooled. The mixture was concentrated in vacuo and the residue was purified by flash chromatography (25%–30% ethyl acetate in hexane) to afford 0.24 g (29%) of 2-(2,6-dichlorophenylcarbonyloxymethyl)-4-propyl-1,2,5 -thiadiazolidin-3-one 1,1-dioxide (Formula I: Ar=2,6-$Cl_2$-phenyl; $R^1$=H; $R^2$=propyl; $R^3$=H) as a solid, m.p.95°–97° C.

EXAMPLE 2

(a)

To a stirred solution of 7.36 ml (84.9 mmol) of chlorosulfonyl isocyanate in 150 ml of methylene chloride was added phenylmethanol (8.82 ml, 84.7 mmol) at 0° C. over a period of 35 minutes. After stirring the above solution for 2 hours at this temperature, a solution of 15.62 g (93.25 mmol) of DL-valine methyl ester hydrochloride in methylene chloride containing triethylamine (36.6 ml) was added at 0°–5° C., and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride (2×200 ml) and the combined organic layer was washed with brine, dried and concentrated in vacuo to yield 30 g of N-(carbobenzyloxyaminosulfonyl)-DL-valine methyl ester(Formula XIV: R=$CH_3$; $R^1$=H; $R^2$=isopropyl; $R^3$=H) as a solid.

(b)

A solution of N-(carbobenzyloxyaminosulfonyl)-DL-valine methyl ester (28.5 g) in methanol (200 ml) under nitrogen was cooled to 0° C. and 1.8 g of 10% Pd/C was added. The mixture was placed into a Parr Apparatus and hydrogenated for 2 hours. The catalyst was removed on a pad of CELITE® and the filtrate was concentrated in vacuo and purified by flash silica gel chromatography (ethyl acetate/hexane, 1:1) to afford 17.2 g (96%) of N-(aminosulfonyl)-DL-valine methyl ester (Formula VII: R=$CH_3$; $R^1$=H; $R^2$=isopropyl; $R^3$=H) as a solid.

(c)

A solution of freshly prepared sodium methoxide (6.41 g, from 2.3 g of Na) in 100 ml of methanol was added to a solution of N-(aminosulfonyl)-DL-valine methyl ester (10.5 g; 0.05 mmol) in methanol (150 ml) and the resulting reaction mixture was stirred for 6 hours. The mixture was cooled, neutralized with BIO-RAD® 50W-X8 $H^+$ ion exchange resin, and filtered. The filtrate was concentrated in vacuo to yield a solid residue which was crystallized from methanol/hexane to afford 16.4 g of a crude 4 -isopropyl-1,2,5-thiadiazolidin-3-one 1,1-dioxide (Formula IV: $R^1$=H $R^2$=isopropyl, $R^3$=H).

(d)

To a mixture of 4-isopropyl-1,2,5-thiadiazolidin-3-one 1,1-dioxide (7.0 g, 39.32 mmol) suspended in 150 ml of toluene was added phenylthiomethyl chloride (6.83 g, 43 mmol) and tetrabutylammonium bromide (1.26 g, 3.93 mmol). The resulting mixture was refluxed for 17 hours, cooled, filtered, and the filtrate was concentrated in vacuo. The residue was purified by column chromatography to afford 5.2 g of 2-phenylthiomethyl-4 -isopropyl-1,2,5-thiadiazolidin-3-one 1,1-dioxide (Formula VI: $R^1$=H; $R^2$=isopropyl; $R^3$=H).

(e)

To a solution of 2-phenylthiomethyl-4-isopropyl-1,2,5 -thiadiazolidin-3-one 1,1-dioxide (3.8 g) in 60 ml of methylene chloride was added sulfuryl chloride (1.52 ml) and the mixture was stirred for 2.5 hours at room temperature. The mixture was concentrated in vacuo, the residue triturated in hexane (200 ml) for 2 hours, and the resulting solid filtered and dried to afford 2.7 g (94%) of 2-chloromethyl-4-isopropyl-1,2,5-thiadiazolidin-3-one 1,1-dioxide (Formula II: $R^1$=H; $R^2$=isopropyl; $R^3$=H; X'=Cl) as a solid, m.p. 71°–72° C.

(f)

A mixture of 2,6-dichlorobenzoic acid (0.44 g; 2.3 mmol), 2 -chloromethyl-4-isopropyl-1,2,5-thiadiazolidin-3-one 1,1-dioxide (0.5 g; 2.2 mmol) and triethylamine (230 mg; 2.3 mmol) in toluene was allowed to reflux for 2.5 hours, and then cooled. The mixture was concentrated in vacuo and the residue was purified by flash silica gel chromatography (25%–30% ethyl acetate in hexane) to afford 0.41 g (49%) of 2-(2,6-dichlorophenylcarbonyloxymethyl)-4 -isopropyl-1,2,5-thiadiazolidin-3-one 1,1-dioxide (Formula I: Ar=2,6-$Cl_2$-phenyl; $R^1$=H; $R^2$=isopropyl; $R^3$=H) as a solid, m.p.151°–152° C.

EXAMPLE 3

(a)

To a stirred solution of 7.36 ml (84.8 mmol) of chlorosulfonyl isocyanate in 150 ml of methylene chloride was added phenylmethanol (8.82 ml, 84.7 mmol) at 0°–5° C. After stirring the above solution for 1.5 hours at this temperature, a solution of 15.62 g (93.25 mmol) of 2-aminopentanoic acid methyl ester hydrochloride in 500 ml of methylene chloride containing triethylamine (25.54 g, 252.8 mmol) was added at 0°–5° C., and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride/ethyl acetate (4:1, 2×200 ml) and the combined organic layer was washed with brine, dried and concentrated in vacuo to yield 33 g of 2-(N-carbobenzyloxyaminosulfonyl)aminopentanoic acid methyl ester (Formula XIV: R=CH$_3$; R$^1$=H; R$^2$=propyl; R$^3$=H) as a solid, m.p. 76°–78° C.

(b)

A solution of 2-(N-carbobenzyloxyaminosulfonyl) aminopentanoic acid methyl ester (33 g) in methanol (250 ml) under nitrogen was cooled to 0° C. and 1.4 g of 10% Pd/C was added. The mixture was placed into a Parr Apparatus and hydrogenated for 2 hours. The catalyst was removed on a pad of CELITE® and the filtrate was concentrated in vacuo and purified by flash silica gel chromatography (50% ethyl acetate in hexane) to afford 13.5 g (76%) of 2-(aminosulfonylamino)pentanoic acid methyl ester (Formula VII: R=CH$_3$; R$^1$=H; R$^2$=propyl; R$^3$=H) as a solid, m.p. 63°–64° C.

(c)

A solution of 2-(aminosulfonylamino) pentanoic acid methyl ester (13 g; 0.05 mmol) in methanol (150 ml) was added to a solution of sodium methoxide (5.54 g, from 2 g of Na) in 150 ml of methanol and the resulting reaction mixture was refluxed for 18 hours. The mixture was cooled, neutralized with BIO-RAD® 50W-X8 H$^+$ ion exchange resin, and filtered. The filtrate was concentrated in vacuo to yield an oil which was crystallized from methanol/hexane to afford 10.8 g (quantitative) of 4-propyl-1,2,5-thiadiazolidin-3-one 1,1-dioxide (Formula IV: R$^1$=H; R$^2$=propyl; R$^3$=H).

(d)

To a mixture of 4-propyl-1,2,5-thiadiazolidin-3-one 1,1-dioxide (5.0 g, 28.25 mmol) suspended in 150 ml of toluene was added phenylmethyl bromide (5.32 g, 31.03 mmol) and tetrabutylammonium bromide (0.9 g, 0.28 mmol). The resulting mixture was refluxed for 19 hours, cooled, filtered, and the filtrate was concentrated in vacuo. The residue was purified by flash chromatography to afford 2.97 g (39%) of 2-phenylmethyl-4 -propyl-1,2,5-thiadiazolidin-3-one 1,1-dioxide (Formula IX: R$^1$=H; R$^2$=propyl) as a solid, m.p., 63.5°–65.5° C.

(e)

Potassium t-butoxide (1.05 g, 9.37 mmol) was added to a solution of 2-phenylmethyl-4-propyl-1,2,5-thiadiazolidin-3-one 1,1-dioxide (2.4 g, 8.95 mmol) in 25 ml of THF at 0° C. and the mixture was stirred at this temperature for 1 hour. To the mixture was added methyl iodide (6.35 g, 44.73 mmol) and the resulting mixture was allowed to stir at 0° C. for 0.5 hour and at room temperature for 4 hours. The resulting mixture was quenched with saturated ammonium chloride, extracted with ethyl acetate and the organic layer was washed with brine. The organic layer was dried, concentrated in vacuo, and the residue was purified by flash chromatography to afford 2.4 g (95%) of 2-phenylmethyl-4-propyl-5 -methyl-1,2,5-thiadiazol-idin-3-one 1,1-dioxide (Formula XI: R$^1$=H; R$^2$=propyl, R$^3$=methyl) as an oil.

(f)

To a suspension of 3.5 g of 10% Pd/C in 150 ml of methanol containing ammonium formate (14 g) was added a solution of 2-phenylmethyl- 4-propyl-5-methyl-1,2,5-thiadiazolidin-3-one 1,1 -dioxide (8.7 g) in 40 ml of methanol. The mixture was stirred at room temperature for 15 hours, filtered through a pad of CELITE®, and the residue was washed with methanol. The combined filtrate was concentrated in vacuo to afford 7.6 g of 4-propyl-5-methyl- 1,2,5-thiadiazolidin-3-one 1,1-dioxide (Formula IV: R$^1$=H, R$^2$=propyl, R$^3$=methyl) as a solid.

(g)

A mixture of 4-propyl-5-methyl-1,2,5-thiadiazolidin-3-one 1,1-dioxide (9 g), phenylthiomethyl chloride (7.43 g) and tetrabutylammonium bromide (1 g) suspended in 200 ml of toluene was refluxed for 8 hours, cooled, and concentrated in vacuo. The residue was purified by flash chromatography (15%–20% ethyl acetate in hexane) to afford 8.5 g (88%) of 2-phenylthiomethyl-4-propyl-5 -methyl-1,2,5-thiadiazolidin-3-one 1,1-dioxide (Formula VI: R$^1$=H; R$^2$=propyl; R$^3$=methyl).

(h)

To a solution of 2-phenylthiomethyl-4-propyl-5-methyl-1,2,5 -thiadiazolidin-3-one 1,1-dioxide (8.4 g) in 150 ml of methylene chloride was added sulfuryl chloride (3.22 ml) and the mixture was stirred for 3 hours at room temperature. The mixture was concentrated in vacuo and the residue triturated in hexane (150 ml) for 2 hours. The solvent was concentrated in vacuo and the residue was purified by falsh chromatography (silica gel) to afford 3.54 g of 2-chloromethyl-4-propyl-5-methyl-1,2,5-thiadiazolidin-3-one 1,1 -dioxide (Formula II: R$^1$=H; R$^2$=propyl; R$^3$=methyl; X'=Cl) as a solid.

(i)

A mixture of 2-chloromethyl-4-propyl-5-methyl-1,2,5 -thiadiazolidin-3-one 1,1-dioxide (0.5 g; 2.08 mmol), 2,6 -dichlorobenzoic acid (0.4 g; 2.09 mmol), and triethylamine (0.3 mL; 2.08 mmol) in 20 ml of toluene was allowed to react at 90°–100° C. for 15 hours and at 100° C. for 19 hours, and then cooled. The mixture was concentrated in vacuo and the residue was purified by flesh chromatography to afford 0.66 g (80%) of 2-(2,6 -dichlorophenylcarbonyloxy-methyl)-4-propyl-5-methyl-1,2,5 -thiadiazolidin-3-one 1,1-dioxide (Formula I: Ar=2,6-Cl$_2$-phenyl; R$^1$=H; R$^2$=propyl; R$^3$=methyl) as an oil.

EXAMPLE 4

(a)

Eight grams (44.94 mmol) of 4-isopropyl-1,2,5-thiadiazolidin- 3-one 1,1-dioxide, phenylmethyl bromide (8.09 g, 47.2 mmol), and tetrabutylammonium bromide (1.5 g, 4.66 mmol) suspended in toluene/DMF (200 ml/50 ml) was allowed to react at 130° C. for 30 hours. The resulting mixture was cooled, the excess toluene was concentrated in vacuo, and the residue was diluted with 200 ml of water and extracted with ether/ethyl acetate (4:1, 700 ml). The organic layer was washed with water and brine, dried and concentrated in vacuo to yield a residue which was purified by flash chromatography to afford 8.6 g (72%) of 2-phenylmethyl-4 -isopropyl-1,2,5-thiadiazol-idin-3-one 1,1-dioxide (Formula IX: R$^1$=H; R$^2$=isopropyl) as a solid.

(b)

To a solution of potassium t-butoxide (3.53 g, 29 mmol) in THF was added a solution of 2-phenylmethyl-4-isopropyl-1,2,5-thiadiazolidin-3-one 1,1-dioxide (7.7 g, 29 mmol) in THF at 0° C and the mixture was stirred at this temperature for 1 hour. To the mixture was added methyl iodide (20.38 g, 0.143 mol) and the resulting mixture was allowed to stir at room temperature for 2.5 hours. The resulting mixture was quenched with brine, extracted with ether, and the organic layer was washed with brine. The organic layer was dried, concentrated in vacuo, and the residue was purified by flash chromatography to afford 7.1 g (88%) of 2-phenylmethyl-4-isopropyl-5-methyl-1,2,5-thiadiazolidin-3-one 1,1-dioxide (Formula XI: $R^1$=H; $R^2$=isopropyl, $R^3$=methyl) as a solid, m.p. 52.5°–54° C.

(c)

To a suspension of 3.5 g of 10% Pd/C in 150 ml of methanol containing ammonium formate (15 g) was added a solution of 2-phenylmethyl-4-isopropyl-5-methyl-1,2,5-thiadiazolidin-3-one 1,1-dioxide (7.1 g) in 50 ml of methanol under nitrogen. The mixture was stirred at room temperature for 7 hours, filtered through a pad of CELITE® and the residue was washed with methanol. The combined filtrate was concentrated in vacuo to afford 4-isopropyl-5-methyl-1,2,5-thiadiazolidin-3-one 1,1-dioxide 2-ammonium salt (Formula IV: $R^1$=H; $R^2$=isopropyl; $R^3$=methyl; as $NH_4^+$ salt).

(d)

A mixture of 4-isopropyl-5-methyl-1,2,5-thiadiazolidin-3-one 1,1-dioxide 2-ammonium salt (5.26 g, 25.2 mmol), phenylthiomethyl chloride (5.6 g, 35.2 mmol) and tetrabutylammonium bromide (0.81 g, 2.51 mmol) suspended in 200 ml of toluene/DMF (3:1) was refluxed for 16 hours, cooled, and concentrated in vacuo. The residue was diluted with 150 ml of water, extracted with ether/ethyl acetate (5:1, 600 ml), and the organic layer was washed with water, brine, and dried. The organic solution was concentrated in vacuo and the residue was purified by flash chromatography to afford 6.47 g (82%) of 2-phenylthiomethyl-4-isopropyl-5-methyl-1,2,5-thiadiazolidin-3-one 1,1-dioxide (Formula VI: $R^1$=H; $R^2$=isopropyl; $R^3$=methyl) as a solid, m.p. 82°–83° C.

(e)

To a solution of 2-phenylthiomethyl-4-isopropyl-5-methyl-1,2,5-thiadiazolidin-3-one 1,1-dioxide (6.38 g, 23.31 mmol) in 150 ml of methylene chloride was added sulfuryl chloride (2.5 ml, 30.4 mmol) and the mixture was stirred for 2 hours at room temperature. The mixture was concentrated in vacuo and the residue triturated in hexane to afford 4.32 g (88%) of 2-chloromethyl-4-isopropyl-5-methyl-1,2,5-thiadiazolidin-3-one 1,1-dioxide (Formula II: $R^1$=H; $R^2$=isopropyl; $R^3$=methyl; X'=Cl) as a solid, m.p. 118.5°–119.5° C.

(f)

To a solution of 2-chloromethyl-4-isopropyl-5-methyl-1,2,5-thiadiazolidin-3-one 1,1-dioxide (0.5 g; 2.08 mmol) in 10 ml of DMF was added at room temperature 2,6-dichlorobenzoic acid (0.44 g; 2.3 mmol), potassium carbonate (0.43 g, 3.1 mmol), and tetrabutylammonium bromide (67 mg; 0.21 mmol) and the resulting solution was allowed to react at 60°–70° C. for 2 hours and then cooled. The mixture was diluted with ice/water, extracted with ether/ethyl acetate (5:1, 400 ml), and the organic layer was washed with water, brine, and dried. The organic solution was concentrated in vacuo and the residue was purified by flash chromatography to afford 0.51 g (62%) of 2-(2,6-dichlorophenylcarbonyloxymethyl)-4-isopropyl-5-methyl-1,2,5-thiadiazolidin-3-one 1,1-dioxide (Formula I: Ar=2,6-$Cl_2$-phenyl; $R^1$=H; $R^2$=isopropyl; $R^3$=methyl) as a solid, m.p. 70°–71.5° C.

EXAMPLE 5

(a)

Potassium t-butoxide (2.3 g, 2.05 mmol) was added to a solution of 2-phenylmethyl-4-propyl-1,2,5-thiadiazolidin-3-one 1,1-dioxide (5 g, 1.56 mmol) in 100 ml of THF at 0° C. and the mixture was stirred at this temperature for 1 hour. To the mixture was added ethyl iodide (11.64 g, 7.46 mmol) at 0° C. and the resulting mixture was allowed to stir at room temperature for 40 hours. The resulting mixture was quenched with brine, extracted with ethyl acetate (150 ml) and the organic layer was washed with brine. The organic layer was dried, concentrated in vacuo, and the residue was purified by flash chromatography to afford 5.27 g of 2-phenylmethyl-4-propyl-5-ethyl-1,2,5-thiadiazolidin-3-one 1,1-dioxide (Formula XI: $R^1$=H; $R^2$=propyl; $R^3$=ethyl) as an oil.

(b)

A mixture of 2 g of 10% Pd/C, ammonium formate (3.35 g), and 2-phenylmethyl-4-propyl-5-ethyl-1,2,5-thiadiazolidin-3-one 1,1-dioxide (5.25 g) in 300 ml of methanol was stirred at room temperature for 20 hours, filtered through a pad of CELITE®, and the residue was washed with methanol. The combined filtrate was concentrated in vacuo to afford 3.8 g of 4-propyl-5-ethyl-1,2,5-thiadiazolidin-3-one 1,1-dioxide ammonium salt (Formula IV: $R^1$=H; $R^2$=propyl; $R^3$=ethyl; as $NH_4^+$ salt) as a solid.

(c)

A mixture of 4-propyl-5-ethyl-1,2,5-thiadiazolidin-3-one 1,1-dioxide (3.7 g, 16.6 mmol), phenylthiomethyl chloride (2.9 g, 18.28 mmol) and tetrabutylammonium bromide (0.53 g, 3.1 mmol) suspended in toluene/DMF (90 ml/10 ml) was refluxed for 8 hours, cooled, and concentrated in vacuo. The residue was diluted with water, extracted with ether/ethyl acetate (500 ml, 1:1), and the organic layer was washed with water and brine. The organic layer was dried, concentrated in vacuo, and the residue was purified by flash chromatography to afford 4.01 g of 2-phenylthiomethyl-4-propyl-5-ethyl-1,2,5-thiadiazolidin-3-one 1,1-dioxide (Formula VI: $R^1$=H; $R^2$=propyl; $R^3$=ethyl) as an oil.

(d)

A solution of 2-phenylthiomethyl-4-propyl-5-ethyl-1,2,5-thiadiazolidin-3-one 1,1-dioxide (3.97 g) and sulfuryl chloride (1.47 ml) in 80 ml of methylene chloride was stirred for 3 hours at room temperature. The mixture was concentrated in vacuo and the residue triturated in hexane. The solvent was concentrated in vacuo and the residue was purified by flash chromatography (silica gel) to afford 2.4 g (77%) of 2-chloromethyl-4-propyl-5-ethyl-1,2,5-thiadiazolidin-3-one 1,1-dioxide (Formula II: $R^1$=H; $R^2$=propyl; $R^3$=ethyl; X'=Cl) as an oil.

(e)

A mixture of 2,6-dichlorobenzoic acid cesium salt (prepared from 0.42 g of the acid and cesium carbonate (0.36 g) in methanol followed by removal of methanol and drying in vacuo) and 2-chloromethyl-4-propyl-5-ethyl-1,2,5-thiadiazolidin-3-one 1,1-dioxide (0.5 g) in DMF was allowed to react at 90°–100° C. for 2 hours, and then cooled. The mixture was diluted with ice/water, extracted with ether/ethyl acetate, and the organic layer was washed with water, brine, and dried. The organic solution was concentrated in vacuo and the residue was purified by flash chromatography to afford 0.64 g (80%) of 2-(2,6-dichloro-phenylcarbonyloxymethyl)-4-propyl- 5-ethyl-1,2,5-thiadiazolidin-3-one 1,1-dioxide (Formula I: Ar=2,6-Cl$_2$-phenyl; R$^1$=H; R$^2$=propyl; R$^3$=ethyl) as an oil.

EXAMPLE 6

(a)

To a stirring mixture of 4-chlorobenzaldehyde (42.2 g, 0.3 mol), DL-alanine methyl ester hydrochloride (42.7 g, 0.306 mol), and 150 g of magnesium sulfate in 1 L of methylene chloride was added 30.3 g (0.3 mol) of triethylamine in 150 ml of methylene chloride in one portion and the resulting mixture was stirred for 20 hours. The reaction mixture was filtered, the filtrate concentrated in vacuo, and the residue (solid and oil) was dissolved in 500 ml of ether. The insoluble solid (triethylamine hydrochloride) was removed by filtration and the filtrate was concentrated in vacuo to afford 64.01 g (94.6%) of N-(4-chlorophenyl)methylene-DL-alanine methyl ester as a yellow oil.

(b)

To a solution of potassium t-butoxide (24.88 g, 0.22 mol) in 450 ml of dry THF cooled to –78° C. under nitrogen was added a solution of N-(4-chlorophenyl)methylene-DL-alanine methyl ester (50 g, 0.222 mol) in 250 ml of THF over a period of 15 minutes. To the resulting red reaction mixture was added with stirring at –78° C. propyl iodide (38.93 g, 0.229 mol) in 150 ml of THF while maintaining the reaction temperature at –60° C.—78° C. Following the addition, the mixture was stirred overnight at room temperature under nitrogen. The reaction mixture was quenched with 250 ml of 1N HCl solution, stirred at room temperature for 1.5 hours, concentrated in vacuo to a volume of 700 ml, and extracted with ether (3×150 ml). The aqueous layer was concentrated in vacuo, the resulting brown oil dissolved in methanol (200 ml), and the methanol solution was filtered. The filtrate was concentrated in vacuo and a brown residual oil was dried in vacuo, dissolved in water, and the solution was extracted with ether. The aqueous layer was concentrated in vacuo to afford, after recrystallization from methanol/ether, 40.33 g of 2-propyl-DL-alanine methyl ester hydrochloride, m.p.25°–256° C.

(c)

To a stirred solution of 15.4 9 ml (0. 178 mol) of chlorosulfonyl isocyanate in methylene chloride was added phenylmethanol (18.5 ml, 0.178 mol) at 0°–5° C. After stirring the above cold solution at this temperature, a solution of 34.9 g (0.192 mol) of 2-propyl-DL-alanine methyl ester hydrochloride in 350 ml of methylene chloride containing triethylamine (73.86 ml, 0.532 mol) was added, and the resulting mixture was stirred for 17 hours allowing the mixture to warm to room temperature. To the reaction mixture was added 500 ml of 10% aq. HCl solution saturated with sodium chloride, and the organic layer was separated. The aqueous layer was extracted with methylene chloride (2×100 ml) and the combined organic layer was dried over magnesium sulfate, concentrated in vacuo, and the residual brown oil was purified by flash chromatography (30% ethyl acetate in hexane) followed by crystallization from ether/hexane to afford 22.35 g (35%) of N-(carbobenzyloxyaminosulfonyl)- 2-propyl-DL-alanine methyl ester (Formula XIV: R=CH$_3$; R$^1$=propyl; R$^2$=CH$_3$; R$^3$=H) as a white solid, m.p. 97°–99° C.

(d)

A mixture of N-(carbobenzyloxyaminosulfonyl)-2-propyl-DL-alanine methyl ester (22.35 g, 62.36 mmol), methanol (200 mL) and 10% palladium on Carbon (1.0 g) was placed on a Parr hydrogenator at 60 psi for 1.5 hours. The reaction mixture was passed through a pad of CELITE®, and the filtrate was concentrated in vacuo to afford 11.16 g (79.8%) of N-aminosulfonyl-2-propyl-DL-alanine methyl ester (Formula VII: R=CH$_3$; R$^1$=propyl; R$^2$=CH3; R$^3$=H).

(e)

A solution of N-(aminosulfonyl)-2-propyl-DL-alanine methyl ester (10.66 g; 47.53 mmol) in methanol (100 ml) was added in one portion to a solution of sodium methoxide (prepared from 2.0 g of Na in 100 ml of dry methanol under nitrogen) and the resulting reaction mixture was stirred for 15 hours. The mixture was neutralized with BIO-RAD® 50W-X8 H$^+$ ion exchange resin with stirring (20 minutes), and filtered. The filtrate was concentrated in vacuo to yield an oil which was dried in vacuo (4 hours) to afford 8.96 g (98%) of 4-methyl-4-propyl-1,2,5-thiadiazolidin-3-one 1,1-dioxide (Formula IV: R$^1$=propyl;R$^2$=CH$_3$; R$^3$=H).

(f)

To a mixture of 4-methyl-4-propyl-1,2,5-thiadiazolidin-3-one 1,1-dioxide (8.25 g, 42.92 mmol) in 80 ml of dry DMF was added phenylmethyl bromide (8.08 g, 47.21 mmol) and tetrabutylammonium bromide (2.08 g, 6.64 mmol) in one portion. The resulting mixture was heated at 120° C. for 8 hours and then stirred at room temperature overnight. The mixture was cooled, poured over ice-water (400 ml), and the mixture was extracted with ethyl acetate (2×250 ml). The organic layer was washed with water and brine, dried over sodium sulfate, and concentrated in vacuo. The brown residual oil was purified by flash chromatography (silica gel; 25% ethyl acetate in hexane) to afford 9.34 g (77.1%) of 2-phenylmethyl-4-methyl-4 -propyl-1,2,5-thiadiazolidin-3-one 1,1-dioxide (Formula IX: R$^1$=propyl; R$^2$=CH$_3$) as an oil.

(g)

Potassium t-butoxide (3.93 g, 35.06 mmol) was added in one portion to a solution of 2-phenylmethyl-4-methyl-4-propyl-1,2,5 -thiadiazolidin-3-one 1,1-dioxide (9 g, 31.87 mmol) in 250 ml of THF at 0° C. and the mixture was stirred under nitrogen at this temperature for 1 hour. To the mixture was added methyl iodide (27.14 g, 191.22 mmol) at 0° C. and the resulting mixture was allowed to stir at 0° C. for ½ hour and at room temperature for 11 hours. The resulting mixture was poured into 400 ml of saturated ammonium chloride solution, extracted with ethyl acetate, and the organic layer was washed with water and brine. The organic layer was dried over sodium sulfate, concentrated in vacuo to afford 9.28 g (98%) of 2-phenylmethyl-4-methyl-4 -propyl-5-methyl-1,2,5-thiadiazolidin- 3-one 1,1-dioxide (Formula XI: $R^1$=propyl; $R^2$=$CH_3$; $R^3$=methyl ) as an oil.

(h)

To a solution of 2-phenylmethyl-4-methyl-4-propyl-5-methyl- 1,2,5-thiadiazolidin-3-one 1,1-dioxide (8.78 g, 29.62 mmol) in 250 ml of dry methanol was added 1.5 g of 10% Pd/C followed by ammonium formate (5.6 g, 88.68 mmol), and the mixture was stirred at room temperature for 4 hours. After adding an additional ammonium formate (2×3 equiv), the mixture was heated at 80°–90° C. overnight, cooled, filtered through a pad of CELITE® and the residue was washed with methanol. The combined filtrate was concentrated in vacuo to afford 5.7 g of 4-methyl-4 -propyl-5-methyl-1,2,5 -thiadiazolidin-3-one 1,1-dioxide (Formula IV: $R^1$=propyl; $R^2$=$CH_3$; $R^3$=CH3) as a solid.

(i)

A mixture of 4-methyl-4-propyl-5-methyl-1,2,5-thiadiazolidin- 3-one 1,1-dioxide (5.44 g, 28.31 mmol), phenylthiomethyl chloride (5.39 g, 33.97 mmol) and tetrabutylammonium bromide (0. 912 g, 2.83 mmol) suspended in DMF (120 ml) was heated at 75° C. for 23 hours, cooled, and poured into 250 ml of ice/water. The mixture was extracted with ethyl acetate (3×150 ml), and the organic layer was washed with water and brine. The organic layer was dried, concentrated in vacuo, and the residue was purified by flash chromatography (silica gel; 10% ethyl acetate in hexane) to afford 1.65 g (17.7%) of 2-phenylthiomethyl-4-methyl-4-propyl-5-methyl- 1,2,5-thiadiazolidin-3-one 1,1-dioxide (Formula VI: $R^1$=propyl; $R^2$=$CH_3$; $R^3$=$CH_3$).

The above aqueous layer was concentrated in vacuo, the residue was triturated with ethyl acetate, and the organic layer was concentrated in vacuo to recover 10 g of a crude 4-methyl-4-propyl- 5-methyl-1,2,5-thiadiazolidin-3-one 1,1-dioxide. Using the recovered material, the above reaction was repeated to afford an additional 5.829 g (63%; total yield=80.4%) of the desired product.

(j)

A solution of 2-Phenylthiomethyl-4-methyl-4-propyl-5-ethyl- 1,2,5-thiadiazolidin-3-one 1,1-dioxide (0.96 g) and sulfuryl chloride (0.28 ml) in 25 ml of dry methylene chloride was stirred for 1.75 hours at room temperature. The mixture was concentrated in vacuo and the residue triturated in 30 ml of hexane to afford 480 mg (64.5%) of 2-chloromethyl-4-methyl-4-propyl-5-methyl-1,2,5 -thiadiazolidin-3-one 1,1-dioxide (Formula II: $R^1$=propyl; $R^2$=$CH_3$; $R^3$=$CH_3$; X'=Cl) as a solid, m.p. 99°–100° C.

(k)

To a stirred solution of 2,6-dichlorobenzoic acid (206 mg, 1.08 mmol) and 112 mg (0.812 mmol) of potassium carbonate in 20 ml of DMF under nitrogen was added 2-chloromethyl-4-methyl-4-propyl-5 -methyl-1,2,5-thiadiazolidin-3-one 1,1-dioxide (250 mg, 0. 981 mmol) and the mixture was allowed to react at room temperature for 12 hours. After adding an additional 2,6-dichlorobenzoic acid (0.038 g) and 0.055 g of potassium carbonate, the mixture was stirred at room temperature for additional 12 hours. The mixture was diluted with ice/water, extracted with ethyl acetate, and the organic layer was washed with water, brine, and dried. The organic solution was concentrated in vacuo and the residue was purified by flash chromatography (silica gel; 10% ethyl acetate in hexane) to afford 266 mg (66%) of 2- (2,6-dichlorophenylcarbonyloxymethyl)-4-methyl-4 -propyl-5-methyl-1,2,5-thiadiazolidin-3-one 1,1-dioxide (Formula I: Ar-2,6-$Cl_2$-phenyl; $R^1$=propyl; $R^2$=$CH_3$; $R^3$=CH3) as a solid, m.p. 93°–95° C.

EXAMPLE 7

(a)

To a solution of N-t-butoxycarbonyl-sarcosine (50 g; 0.264 mol) in 700 ml of benzene was added 1,8-diazabicyclo [5.4.0] -undec- 7-ene (DBU; 40.19 g, 0.264 mol) in one portion. To the above clear solution was added 74.84 g (0.528 mol) of methyl iodide in one portion and the resulting clear solution was allowed to reflux for 7 hours. After adding additional methyl iodide (16 ml), the reaction mixture was refluxed with stirring and then cooled to room temperature, and stirred overnight. The reaction mixture was filtered, the residue washed with ether, and the combined filtrate was washed with water, saturated sodium bicarbonate solution, and brine. The resulting organic layer was dried over sodium sulfate, filtered, and concentrated in vacuo to afford 46.38 g (86.4 %) of N-t-butoxycarbonyl-sarcosine methyl ester as a yellow oil.

(b)

A 2 M solution of LDA (67.61 ml, 0. 135 mol) was added (via syringe) to a solution of N-t-butoxycarbonyl-sarcosine methyl ester (24.96 g, 0.1279 mol) in 40 ml of dry THF at −78° C. under nitrogen, and the mixture was stirred at this temperature for 30 minutes. To the above mixture was added 4-bromo-2-methyl-2-butene (19.23 g, 0.129 mol) with stirring at −78° C., and the resulting mixture was allowed to warm to room temperature. The reaction mixture was quenched with 6 ml of saturated ammonium chloride solution at −78° C., 20 ml of water added, and the resulting reaction mixture was extracted with ethyl acetate. The organic layer was washed with water and brine, dried over sodium sulfate, and concentrated in vacuo to yield a yellow oil, which was partially purified by silica gel column chromatography (20% ethyl acetate in hexane). The product was then dissolved in 400 ml of ethereal HCl and stirred for 24 hours. The solid product was filtered, the residue washed with ether, and dried in vacuo to afford 15.69 g (61.5 %) of 2-(3-methyl-3-chlorobutyl)-sarcosine methyl ester hydrochloride (Formula XIII: R=$CH_3$; $R^1$=H; $R^2$=$(CH_2)_2C(Cl)(CH_3)_2$; $R^3$=$CH_3$; $X^-$=$Cl^-$) as a solid.

(c)

To a stirred solution of 5.04 ml (58.13 mmol) of chlorosulfonyl isocyanate in methylene chloride was added under nitrogen phenylmethanol (6.02 ml, 58.13 mmol) at 0°–5° C. After stirring the above solution for 1 hour, a solution of 13.28 g (54.39 mmol) of 2-( 3-methyl-3-chlorobutyl)-sarcosine methyl ester hydrochloride in methylene chloride containing triethylamine (24.33 ml, 173.28 mmol) was added at 0°–5° C. and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride and the combined organic layer was washed with brine, dried over magnesium sulfate, and concentrated in vacuo. The residue was purified by silica gel column chromatography (30% ethyl acetate in hexane)

to yield 24.31 g (94.3%) of N-(carbobenzyloxyaminosulfonyl)-2-(3-methyl-3-chlorobutyl)-sarcosine methyl ester (Formula XIV: R=CH$_3$; R$^1$=H; R$^2$=(CH$_2$)$_2$C(Cl)(CH$_3$)$_2$; R$^3$=CH$_3$) as a white solid, m.p. 77°–78° C.

(d)

A solution of N-(carbobenzyloxyaminosulfonyl)-2-(3-methyl-3-chlorobutyl)-sarcosine methyl ester (23.61 g, 55.96 mmol) in 200 ml of methanol under nitrogen was cooled to 0° C. and 1.0 g of 10% Pd/C was added. The mixture was placed into a Parr Apparatus and hydrogenated at 50 psi for 4 hours. The catalyst was removed on a pad of CELITE® and the filtrate was concentrated in vacuo to afford 15.23 g (94.9%) of N-(aminosulfonyl)-2-(3-methyl-3-chlorobutyl)-sarcosine methyl ester (Formula VII: R=CH$_3$; R$^1$=H; R$^2$=(CH$_2$)$_2$C (Cl) (CH$_3$)$_2$; R$^3$=CH$_3$) as an oil.

(e)

A solution of N-(aminosulfonyl)-2-(3-methyl-3-chlorobutyl) sarcosine methyl ester (14.5 g, 50.56 mmol) in methanol (150 ml) was added to a solution of sodium methoxide (Na=2.4 g) in 150 ml of ice-cold methanol. The resulting reaction mixture was stirred at room temperature under nitrogen for 1.5 hours, and the mixture was treated with 25 g of ion-exchange resin (BIO-RAD® 50W- x8 H$^+$) for 40 minutes and filtered. The filtrate was concentrated in vacuo to afford 12.54 g (97.4%) of 4-(3-methyl-3-chlorobutyl)-5-methyl-1,2,5-thiadiazolidin-3-one 1,1-dioxide (Formula IV: R$^1$=H; R$^2$=(CH$_2$)$_2$C(Cl) (CH$_3$)$_2$; R$^3$=CH$_3$) as a solid.

(f)

A mixture of 4-(3-methyl-3-chlorobutyl)-5-methyl-1,2,5-thiadiazolidin-3-one 1,1-dioxide (2.5 g, 9.81 mmol), phenylthiomethyl chloride (2.18 g, 13.74 mmol) and tetrabutylammonium bromide (0.369 g, 1.145 mmol) suspended in 150 ml of DMF was heated at 100° C. for 18 hours. After adding additional TBAB (0.369 g), the mixture was stirred at 95° C. for 4 hours, cooled, and poured into ice/water. The reaction mixture was extracted with ethyl acetate and the organic layer was washed with water and brine, and dried over sodium sulfate. The organic layer was concentrated in vacuo and the residue was purified by silica column chromatography (15% ethyl acetate in hexane) to afford 1.396 g (39%) of 2-phenylthiomethyl-4-(3-methyl-3-chlorobutyl)-5-methyl-1,2,5-thiadiazolidin-3-one 1,1-dioxide (Formula VI: R$^1$=H; R$^2$=(CH$_2$)$_2$C(Cl) (CH$_3$)$_2$; R$^3$=CH$_3$) as a solid.

(g)

To a solution of 2-phenylthiomethyl-4-(3-methyl-3-chlorobutyl)-5-methyl-1,2,5-thiadiazolidin-3-one 1,1-dioxide (1.396 g, 3.82 mmol) in 30 ml of methylene chloride was added sulfuryl chloride (0.366 ml, 4.58 mmol) and the mixture was stirred for 2 hours at room temperature. The mixture was concentrated in vacuo and the residue was purified by silica column chromatography (10% ethyl acetate in hexane) to afford 410 mg (35.4%) of 2-chloromethyl-4-(3-methyl-3-chlorobutyl)-5-methyl-1,2,5-thiadiazolidin-3-one 1,1-dioxide (Formula II: R$^1$=H; R$^2$=(CH$_2$)$_2$C(Cl) (CH$_3$)$_2$; R$^3$=CH$_3$; X'=Cl).

(h)

To a solution of 2-chloromethyl-4-(3-methyl-3-chlorobutyl)-5-methyl-1,2,5-thiadiazolidin-3-one 1,1-dioxide (0.41 g; 1.35 mmol) in DMF was added at room temperature 2,6-dichlorobenzoic acid (0.283 g; 1.48 mmol) and potassium carbonate (0.246 g, 1.78 mmol), and the resulting solution was allowed to react at room temperature for 40 hours. The mixture was poured into ice/water, extracted with ethyl acetate, and the organic layer was washed with water, brine, and dried. The organic solution was concentrated in vacuo and the residue was purified by silica column chromatography to afford 62 mg (10%) of 2-(2,6-dichlorophenylcarbonyloxymethyl)-4-(3-methyl-3-chlorobutyl)-5-methyl-1,2,5-thiadiazolidin-3-one 1,1-dioxide (Formula I: Ar=2, 6-Cl$_2$-phenyl; R$^1$=H; R$^2$=(CH$_2$)$_2$C (Cl) (CH$_3$)$_2$; R$^3$=CH$_3$) as a gum.

EXAMPLE 8

(a)

A 2 M solution of LDA (70.32 ml, 0.14 mol) was added (via syringe) to a solution of N-t-butoxycarbonyl-sarcosine methyl ester (26 g, 0.1279 mol) in 40 ml of dry THF at −78° C. under nitrogen and the mixture was stirred at this temperature for 30 minutes. To the above mixture was added 4-bromo-2-methyl-2-butene (20 g, 0.134 mol) with stirring continuing at −78° C., and the resulting mixture was allowed to warm to room temperature. The reaction mixture was quenched with 6 ml of saturated ammonium chloride solution at −78° C., 20 ml of water added, and the resulting reaction mixture was extracted with ethyl acetate. The organic layer was washed with water and brine, dried over sodium sulfate, and concentrated in vacuo to yield a yellow oil, which was purified by silica gel column chromatography (20% ethyl acetate in hexane) to afford 22.1 g (63.7 %) of N-t-butoxycarbonyl-2-(3-methyl-2-butenyl)-sarcosine methyl ester as an oil.

(b)

A solution of N-t-butoxycarbonyl-2-(3-methyl-2-butenyl) sarcosine methyl ester (22.1 g, 81.44 mmol) in 400 ml of methanol under nitrogen was cooled to 0° C. and 1.5 g of 10% Pd/C was added. The mixture was placed into a Parr Apparatus and hydrogenated at 50 psi for 6 hours. The catalyst was removed on a pad of CELITE® and the filtrate was concentrated in vacuo to afford 22.04 g (99%) of N-t-butoxycarbonyl-2-(3-methylbutyl)-sarcosine methyl ester as an oil.

(c)

A mixture of N-t-butoxycarbonyl-2-(3-methylbutyl)-sarcosine methyl ester (22.04 g, 80.62 mmol) in 360 ml of ethereal HCl was stirred at room temperature for 3 days. The resulting mixture was cooled in an ice/bath and then the solvent was concentrated in vacuo to afford after drying, 13.17 g (78%) of 2-(3-methylbutyl)-sarcosine methyl ester hydrochloride (Formula XIII: R=CH$_3$; R$^1$=H; R$^2$=(CH$_2$)$_2$CH(CH$_3$)$_2$; R$^3$=CH$_3$; X'=Cl$^-$) which was recrystallized from methanol/ether, m.p. 110°–111° C.

(d)

To a stirred solution of 5.77 ml (66.78 mmol) of chlorosulfonyl isocyanate in methylene chloride was added under nitrogen phenylmethanol (6.89 ml, 66.57 mmol) at 0°–10°

C. After stirring the above solution for 1 hour, a solution of 13.166 g (62.78 mmol) of 2-(3-methylbutyl)-sarcosine methyl ester hydrochloride in methylene chloride containing triethylamine (27.33 ml, 194.62 mmol) was added at 0°–10° C., and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride and the combined organic layer was washed with brine, dried over magnesium sulfate, and concentrated in vacuo to yield 21.22 g (87.2%) of N-(carbobenzyloxyaminosulfonyl)- 2-(3-methylbutyl)-sarcosine methyl ester (Formula XIV: R=CH$_3$; R$^1$=H; R$^2$=(CH$_2$)$_2$CH(CH$_3$)2; R$^3$=CH$_3$ ) as an oil after purification by silica column chromatography (20% ethyl acetate in hexane).

(e)

A solution of (N-carbobenzyloxyaminosulfonyl) -2- (3 -methylbutyl)-sarcosine methyl ester (20.6 g, 53.17 mmol) in 200 ml of methanol under nitrogen was cooled to 0° C. and 1.5 g of 10% Pd/C was added. The mixture was placed into a Parr Apparatus and hydrogenated for 3.5 hours. The catalyst was removed on a pad of CELITE® and the filtrate was concentrated in vacuo to afford 13.24 g (98.6%) of N-aminosulfonyl) -2-(3-methylbutyl)-sarcosine methyl ester (Formula VII: R=CH$_3$; R$^1$=H; R$^2$=(CH$_2$)$_2$CH(CH$_3$)$_2$; R$^3$=CH$_3$ ) as an oil.

(f)

A solution of N-(aminosulfonyl)-2-(3-methylbutyl)-sarcosine methyl ester (12.28 g, 48.67 mmol) in methanol (150 ml) was added under nitrogen to a solution of sodium methoxide (Na=2.1 g, 95.71 mmol) ) in 150 ml of ice-cold methanol. The resulting reaction mixture was stirred at room temperature under nitrogen for 1.5 hours, and the mixture was treated with 25 g of ion-exchange resin (BIO-RAD 50W-x8 H$^+$) for 40 minutes, and filtered. The filtrate was concentrated in vacuo to afford 10.7 g (99.8%) of 4-(3 -methylbutyl)-5-methyl-1,2,5-thiadiazolidin-3-one 1,1-dioxide (Formula IV: R$^1$=H; R$^2$=(CH$_2$)$_2$CH (CH$_3$)$_2$; R$^3$=CH$_3$) as a solid, m.p. 212°–214° C.

(g)

A mixture of 4-(3-methylbutyl)-5-methyl-1,2,5-thiadiazolidin- 3-one 1,1-dioxide cesium salt (prepared by reacting 7.7 g (34.95 mmol) of the dioxide in methanol with 5.13 g of Cs$_2$CO$_3$ followed by removal of solvent) and phenylthiomethyl chloride (6.65 g, 41.94 mmol) suspended in DMF was heated at 85° C. for 17 hours. The mixture was cooled, and poured into 300 ml of ice/water. The reaction mixture was extracted with ethyl acetate (3x) and the organic layer was washed with water and brine and dried over sodium sulfate. The organic layer was concentrated in vacuo and the residue was purified by silica column chromatography (10% ethyl acetate in hexane) to afford 8.15 g (70.6%) of 2-phenylthiomethyl-4-(3 -methylbutyl)-5-methyl-1,2,5-thiadiazolidin-3-one 1,1-dioxide (Formula VI: R$^1$=H; R$^2$=(CH$_2$)$_2$CH(CH$_3$)$_2$; R$^3$=CH$_3$) as an oil.

(h)

To a solution of 2-phenylthiomethyl-4-(3-methylbutyl)-5 -methyl-1,2,5-thiadiazolidin-3-one 1,1-dioxide (8.15 g, 24.66 mmol) in 200 ml of methylene chloride was added in one portion under nitrogen sulfuryl chloride (2.36 ml, 29.6 mmol) and the mixture was stirred for 3.5 hours at room temperature. The mixture was concentrated in vacuo and the residue was triturated in hexane to afford 4.64 g (70%) of 2-chloromethyl-4-(3-methylbutyl)-5-methyl- 1,2:5-thiadiazolidin-3-one 1,1-dioxide (Formula II: R$^1$=H; R$^2$=(CH$_2$)$_2$CH(CH$_3$)$_2$; R$^3$=CH$_3$; X'=Cl) as a solid, m.p. 59°–60° C.

(i)

To a solution of 2,6-dichlorobenzoic acid cesium salt (prepared by reaction of the acid (0.462 g, 2.42 mmol) in methanol with C$_2$CO$_3$ (0.414 g) followed by removal of the solvent) in 25 ml of DMF was added 2-chloromethyl-4-(3-methylbutyl) -5-methyl-1,2,5 -thiadiazolidin-3-one 1,1-dioxide (0.5 g; 1.86 mmol) at room temperature. The resulting solution was allowed to react at room temperature under nitrogen for 26 hours. The mixture was concentrated in vacuo and the residue was dissolved in ethyl acetate and purified by passing through silica column followed by flash chromatography (15% ethyl acetate in hexane ) to afford 610 mg (77.5%) of 2-(2,6-dichlorophenylcarbonyloxymethyl-4-(3-methylbutyl)- 5-methyl-1,2,5-thiadiazolidin-3-one 1,1-dioxide (Formula I: Ar=2,6-Cl$_2$-phenyl; R$^1$=H; R$^2$=(CH$_2$)$_2$CH(CH$_3$)$_2$; R$^3$=CH$_3$) as a gum.

EXAMPLE 9

(a)

To a solution of 2,6-dichloro-3-(hydroxy)benzoic acid methyl ester (38.77 g, 0.176 mol) in DMF was added with stirring under nitrogen 60.95 g (0.441 mol) of potassium carbonate in one portion. The resulting mixture was stirred at room temperature for 15 minutes, 35.87 g (0.211 mol) of 1-(2-chloroethyl)pyrrolidine hydrochloride was added in one portion and the mixture was heated on a steam-bath for 2 hours. The reaction mixture was poured into 900 ml of ice/water, extracted with ethyl acetate (3×450ml), and the organic layer was washed with 5% NaOH solution (125ml), water (125ml), and brine (125ml). The organic layer was dried over sodium sulfate, concentrated in vacuo and the brown residue (95.01 g) was dissolved in 55 ml of ether and treated with ethereal HCl (4.3 N) with stirring. The solid product was filtered and washed with ether to afford 26.221 g (54.4%) of 2; 6-dichloro-3-(2-pyrrolidinoethoxy)benzoic acid methyl ester hydrochloride as a grey solid.

(b)

To a solution of NaOH (2.73 g, 68.25 mmol) in 80 ml of water and 40 ml of methanol was added in one portion 8 g (22.56 mmol) of 2,6-dichloro-3-(2-pyrrolidinoethoxy)benzoic acid methyl ester hydrochloride and the mixture was heated at 90° C. for 15 hours. The mixture was concentrated in vacuo to remove methanol, the aqueous layer was acidified with 20 ml of conc. HCl solution, and the white solid was filtered. The white solid was dissolved in hot water, filtered, and the filtrate was treated with 15 ml of conc. HCl solution. The solid product was recrystallized from methanol/ether to afford 6.53 g (85%) of 2,6-dichloro-3-(2-pyrrolidinoethoxy)benzoic acid hydrochloride (Formula III: Ar=2,6-Cl$_2$-3- (OCH$_2$CH$_2$-1 -pyrrolidinyl)phenyl) as a white crystalline solid, m.p. 257°–259° C.

(c)

To a solution of 2,6-dichloro-3-(2-pyrrolidinoethoxy)-benzoic acid cesium salt (prepared by reaction of the acid (1.045 g, 3.069 mmol) in 30 ml of methanol with $Cs_2CO_3$ (1.2 g) followed by removal of the solvent) in DMF was added 2-chloromethyl-4-(3-methylbutyl)- 5-methyl-1,2,5-thiadiazolidin-3-one 1,1-dioxide (0.75 g; 1.86 mmol) at room temperature. The resulting solution was allowed to react at room temperature under nitrogen for 17 hours. The mixture was concentrated in vacuo and the residue was dissolved in 70% ethyl acetate in ether, filtered, and washed with sodium bicarbonate solution and dried over sodium sulfate. The organic solution was concentrated, the residual clear oil dissolved in 40 ml of ether and treated with ether/HCl. The salt was purified from methanol/ether to afford 2-(2,6-dichloro-3-(2-pyrrolidinoethoxy)phenylcarbonyloxymethyl)- 4-(3-methylbutyl)-5 -methyl-1,2,5-thiadiazolidin-3-one 1,1-dioxide hydrochloride (Formula I: Ar=2, 6-$Cl_2$-3-($OCH_2CH_2$-1-pyrrolidinyl)phenyl; $R^1$=H; $R^2$=$(CH_2)_2CH(CH_3)_2$; $R^3$=$CH_3$; as HCl salt) a solid, m.p. 161°–162° C.

EXAMPLE 10

(a)

To a solution of NaOH (115,2 g) in 800 ml of water/methanol was added in one portion 48.1 g (0.115 mol) of 2,6-dichloro-3-[2-( 4-morpholino) ethoxy]benzoic acid methyl ester hydrochloride and the mixture was heated on a steam/bath for 24 hours. The mixture was concentrated in vacuo to remove methanol, 220 ml of ethanol was added and cooled (5° C.). The white solid was filtered, and washed with cold water followed by ethyl acetate to afford 43 g of 2,6 -dichloro-3-[2- (4-morpholino]ethoxy]benzoic acid (Formula III: Ar=2,6-$Cl_2$-3-($OCH_2CH_2$-4-morpholinyl) phenyl) as a white crystalline solid, m.p. 254°–255° C.

(b)

To a solution of 2,6-dichloro-3-[2-(4-morpholino)ethoxy] benzoic acid cesium salt (prepared by reaction of the acid (0.775 g, 2.42 mmol) in 30 ml of dry methanol with $Cs_2CO_3$ (0.414 g, 1.27 mmol) followed by removal of the solvent) in DMF was added 2 -chloromethyl-4-(3-methylbutyl)-5-methyl-1,2,5-thiadiazolidin-3-one 1,1-dioxide (0.5 g; 1.86 mmol) at room temperature. The resulting solution was allowed to react at room temperature under nitrogen for 17 hours. The mixture was concentrated in vacuo, the residue was dissolved in 150 ml of ethyl acetate, and the organic layer was washed with water, sodium bicarbonate solution, brine and dried over sodium sulfate. The organic solution was concentrated, the residual clear oil was treated in ether with ethereal HCl solution, the solvent concentrated in vacuo, and the resulting solid crystallized from methanol/ether to afford 1.095 g (45.3%) of 2-( 2,6-dichloro-3-[2-( 4 -morpholino)ethoxy]phenyl-carbonyloxymethyl)- 4-(3-methylbutyl)-5-methyl-1,2,5-thiadiazolidin-3-one 1,1-dioxide (Formula I: Ar=2,6-$Cl_2$-3-($OCH_2CH_2$-4-morpholinyl)phenyl; $R^1$=H; $R^2$=$(CH_2)_2CH(CH_3)_2$; $R^3$=$CH_3$; as HCl salt) a solid, m.p. 114°–117° C.

EXAMPLE 11

(a)

To a stirred solution of 21.19 ml (244 mmol) of chlorosulfonyl isocyanate in 1000 ml of methylene chloride was added dropwise under nitrogen phenylmethanol (25.41 ml, 244 mmol) at 0° C. After stirring the above solution for 1.5 hours at 0° C., a solution of 50 g (232 mmol) of DL-phenylalanine methyl ester hydrochloride in 500 ml of methylene chloride containing triethylamine (72.75 g, 719 mmol) was added dropwise with stirring at 0° C., and the resulting mixture was stirred for 3.5 hours allowing the mixture to warm to room temperature. The reaction mixture was washed with 500 ml of 10% aq. HCl solution, saturated with sodium chloride, and the organic layer was separated. The organic layer was dried over sodium sulfate and concentrated in vacuo. The residual oil product was dissolved in ethyl acetate and passed through a plug of silica gel, and the solvent was concentrated in vacuo to yield 91.04 g of N-(carbobenzyloxyaminosulfonyl)-DL-phenylalanine methyl ester(Formula XIV: R=$CH_3$; $R^1$=H; $R^2$=$CH_2Ph$; $R^3$=H) as an oil.

(b)

A solution of 2-(N-carbobenzyloxyaminosulfonyl)-DL-phenylalanine methyl ester (42.76 g, 109 mmol) in ethanol (250 ml) under nitrogen was cooled to 0° C. and 2.5 g of 10% Pd/C was added. The mixture was placed into a Parr Apparatus and hydrogenated for 4 hours at 50 psi. After adding an additional 10% Pd/C (2 g), the mixture was hydrogenated for an additional 3 hours. The catalyst was removed on a pad of CELITE® and the filtrate was concentrated in vacuo and purified by flash silica gel chromatography to afford 26.8 g (95.2%) of N-(aminosulfonyl)-DL-phenylalanine methyl ester (Formula VII: R=$CH_3$; $R^1$=H; $R^2$=$CH_2Ph$; $R^3$=H) as a white solid.

(c)

To a solution of sodium methoxide (from 4.18 g of Na, 182 mmol) in methanol was added in one portion at room temperature under nitrogen 2-(aminosulfonyl)-DL-phenylalanine methyl ester (26.1 g; 101 mmol) and the resulting reaction mixture was stirred for 3.5 hours. The mixture was concentrated in vacuo, the residual white solid treated with 1 N HCl solution, and the solid was filtered. The aqeous filtrate was extracted with ethyl acetate, the organic layer dried over sodium sulfate, and concentrated in vacuo to afford 19.27 g (84.7%) of 4-phenylmethyl-1,2,5 -thiadiazolidin-3-one 1,1-dioxide (Formula IV: $R^1$=H; $R^2$=$CH_2Ph$; $R^3$=H), as a white solid.

(d)

To a mixture of 4-phenylmethyl-1,2,5-thiadiazolidin-3-one 1,1-dioxide cesium salt (prepared by reacting 11.43 g (50.52 mmol) of the dioxide in methanol with 8.23 g (25.26 mmol) of $Cs_2CO_3$ followed by removal of the solvent) in 150 ml of DMF was added in one portion phenylthiomethyl chloride (8.82 g, 55.57 mmol) and the mixture was heated at 80°–90° C. under nitrogen for 17 hours. The mixture was cooled and poured into 600 ml of ice/water. The reaction mixture was extracted with ethyl acetate (3x), the organic layer was dried over sodium sulfate, and concentrated in vacuo. The residual yellow oil was purified by silica column chromatography (5%–10% ethyl acetate in hexane) to afford 16.88 g (95.9%) of 2-phenylthiomethyl-4-phenylmethyl-1, 2,5-thiadiazolidin- 3-one 1,1-dioxide (Formula VI: $R^1$=H; $R^2$=$CH_2Ph$; $R^3$=H) as an yellow oil.

(e)

Potassium t-butoxide (5.65 g, 50.35 mmol) was added to a solution of 2-phenylthiomethyl-4-phenylmethyl-1,2,5-thiadiazolidin- 3-one 1,1-dioxide (14.61 g, 41.93 mmol) in 250 ml of THF at 0° C. and the mixture was stirred at this temperature for ½ hour. To the above mixture was added methyl iodide (35.69 g, 251.58 mmol) at 0° C. and the resulting mixture was allowed to stir for 4.5 hours at room temperature. The resulting mixture was quenched with saturated ammonium chloride solution, extracted with ethyl acetate and the organic layer was washed with brine. The organic layer was dried, concentrated in vacuo, and the residue was purified by flash chromatography to afford 12.53 g (82.4%) of 2-phenylthiomethyl-4 -phenylmethyl-5-methyl-1,2,5-thiadiazolidin-3-one 1,1-dioxide as a yellow solid.

(f)

To a solution of 2-phenylthiomethyl-4-phenylmethyl-5-methyl- 1,2,5-thiadiazolidin-3-one 1,1-dioxide (11.78 g, 33.05 mmol) in 200 ml of methylene chloride was added in one portion under nitrogen sulfuryl chloride (3.15 ml, 39.66 mmol) and the mixture was stirred for 3.5 hours at room temperature. The mixture was concentrated in vacuo and the residue was triturated in hexane and purified by flash chromatography (20% ethyl acetate in hexane) to afford 8.82 g (92.4%) of 2-chloromethyl-4-phenylmethyl-5-methyl-1,2,5 -thiadiazolidin-3-one (Formula II: $R^1$=H; $R^2$=$CH_2Ph$; $R^3$=$CH_3$; X'=Cl) as an oil.

(g)

To a solution of 2,6-dichlorobenzoic acid cesium salt (prepared by reaction of the acid (1.98 g, 10.39 mmol) in methanol with $Cs_2CO_3$ (1.69 g, 5.19 mmol) followed by removal of the solvent) in 25 ml of DMF was added 2-chloromethyl-4-phenylmethyl-5-methyl- 1,2,5-thiadiazolidin-3-one 1,1-dioxide (2 g, 6.93 mmol) at room temperature. The resulting solution was allowed to react at room temperature under nitrogen for 26 hours. The mixture was concentrated in vacuo, the residue was dissolved in ethyl acetate and purified by flash chromatography on silica gel (30% ethyl acetate in hexane ) to afford, after recrystallization from methanol/water, then ether/hexane, 2.78 g (90.6%) of 2-(2,6 -dichloro-phenylcarbonyloxymethyl )-4-phenylmethyl-5-methyl-1,2,5 -thiadiazolidin-3-one 1,1-dioxide (Formula I: Ar=2, 6-$Cl_2$-phenyl; $R^1$=H; $R^2$=$CH_2Ph$; $R^3$=$CH_3$) as a solid, m,p, 96°–98° C.

EXAMPLE 12

To a suspension of 2, 6-dichloro-3- [2-(4-morpholino)ethoxy]benzoic acid cesium salt (prepared by reaction of the acid (2.1 g, 6.56 mmol) in dry methanol with $Cs_2CO_3$ (1.06 g, 3.25 mmol) followed by removal of the solvent) in 30 ml DMF was added 2-chloromethyl-4-propyl- 5-ethyl-1,2,5-thiadiazolidin-3-one 1,1-dioxide (1.2 g, 4.71 mmol) at room temperature. The resulting solution was allowed to react at 80° C. under nitrogen for 2.5 hours. The mixture was poured into ice/water, extracted with ether/ethyl acetate (4:1; 300ml), and the organic layer was washed with water and brine, and dried over sodium sulfate. The organic solution was concentrated in vacuo and the residue was purified by flash chromatography on silica gel to afford 1 g (39%) of 2-(2, 6-dichloro-3- [2-(4-morpholino) ethoxy]phenylcarbonyloxymethyl)-4-propyl-5-ethyl- 1,2,5-thiadiazolidin-3-one 1,1-dioxide, as an oil. The free base (1 g) was converted to the corresponding mesylate salt in isopropanol and was recrystallized from ether/hexane to afford 0.74 g of 2-(2,6- dichloro-3- [2- (4-morpholino]ethoxy] -phenylcarbonyloxymethyl)-4-propyl-5-ethyl-1,2,5-thiadiazolidin-3-one 1,1-dioxide methanesulfonate (Formula I: Ar=2,6-$Cl_2$-3-($OCH_2CH_2$- 4-morpholinyl)phenyl; $R^1$=H; $R^2$=propyl; $R^3$=ethyl; as $CH_3SO_3H$ salt) as a solid, m.p. 142°–145° C.

EXAMPLE 13

(a)

To a stirred solution of 7.36 ml (85 mmol) of chlorosulfonyl isocyanate in 180 ml of methylene chloride was added phenylmethanol (8.82 ml, 85 mmol) at 0° C. over a period of 35 minutes. After stirring the above solution for 2 hours at this temperature, a solution of 16.65 g (93 mmol) of 2-piperidinecarboxylic acid methyl ester hydrochloride in methylene chloride (500 ml) containing triethylamine (35.3 ml) was added at 0°–5° C., and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride (2×200 ml) and the combined organic layer was washed with brine, dried and concentrated in vacuo to yield 31 g of N-(carbobenzyloxyaminosulfonyl)-2-piperidinecarboxylic acid methyl ester(Formula XIV: R=$CH_3$; $R^1$=H; $R^2$ and $R^3$ together =-($CH_2$)4-) as a solid.

(b)

A solution of N-(carbobenzyloxyaminosulfonyl)-2-piperidinecarboxylic acid methyl ester (28.8 g) in methanol (300 ml) under nitrogen was cooled to 0° C. and 1.8 g of 10% Pd/C was added. The mixture was placed into a Parr Apparatus and hydrogenated for 2 hours at 55 psi. The catalyst was removed on a pad of CELITE® and the filtrate was concentrated in vacuo and purified by flash silica gel chromatography (35%–40% ethyl acetate/hexane) to afford 17 g (90%) of N-(aminosulfonyl)-2 -piperidinecarboxylic acid methyl ester (Formula VII: R=$CH_3$; $R^1$=H; $R^2$ and $R^3$ together =-($CH_2$)4-) as a solid, m.p. 72°–74° C.

(c)

To a solution of freshly prepared sodium methoxide (6.05 g, from 2.1 g of Na) in 150 ml of methanol was added a solution of N-(aminosulfonyl )-2-piperidinecarboxylic acid methyl ester (15 g; 0.067 mmol) in methanol (100 ml) and the resulting reaction mixture was stirred at room temperature for 2 hours. The mixture was cooled, neutralized with BIO-RAD® 50W-X8 H$^+$ ion exchange resin, and filtered. The filtrate was concentrated in vacuo to afford 14.4 g of 1,2,5-thiadiazolo[2,3-a]3,3a,4,5,6,7-hexahydropyridine-3-one 1,1-dioxide (Formula IV: $R^1$=H; $R^2$ and $R^3$ together =-($CH_2$)4-).

(d)

To a mixture of 1,2,5-thiadiazolo[2,3-a]3,3a,4,5,6,7 -hexahydropyridine-3-one 1,1-dioxide (10.0 g, 52 . 6 mmol) suspended in 400 ml of toluene was added phenylthiomethyl chloride (10.85 g, 68.4 mmol) and tetrabutylammonium bromide (1.69 g) . The resulting mixture was refluxed for 6 hours, cooled, filtered, and the filtrate was concentrated in vacuo. The residue was purified by flash column chromatography (25% ethyl acetate in hexane) to afford 12.83 g (78%) of 2-phenylthiomethyl-1,2,5-thiadiazolo [2,3-a]3,3a, 4,5,6,7-hexahydropyridine-3-one 1,1-dioxide (Formula VI: $R^1$=H; $R^2$ and $R^3$ together =-($CH_2$)$_4$-) as an oil.

(e)

To a solution of 2-phenylthiomethyl-1,2,5-thiadiazolo[2,3-a]3, 3a, 4,5,6,7-hexahydropyridine-3-one 1,1-dioxide (12 g) in 250 ml of methylene chloride was added sulfuryl chloride (4.63 ml) and the mixture was stirred for 3 hours at room temperature. The mixture was concentrated in vacuo, the residue triturated in hexane (200 ml) for 2 hours, the resulting solid filtered and washed with hexane to afford, after drying, 8.1 g (88%) of 2-chloromethyl-1,2,5-thiadiazolo[2,3-a]3,3a,4,5,6,7-hexahydropyridine-3-one 1,1-dioxide (Formula II: $R^1$=H; $R^2$ and $R^3$ together =-($CH_2$)4-; X'=Cl) as a solid, m.p. 124°–125.5° C.

(f)

A mixture of 2,6-dichlorobenzoic acid (0. 404 g), 2-chloromethyl-1,2,5-thiadiazo [2,3-a]3,3a,4,5, 6,7-hexahydropyridine- 3-one 1,1-dioxide (0.5 g), and triethylamine (0.21 g) in toluene (15 ml) was allowed to reflux for 6 hours and then cooled. The mixture was concentrated in vacuo and the residue was purified by silica gel chromatography to afford 0.43 g (52%) of 2-(2,6-dichlorophenylcarbonyloxymethyl)- 1,2,5-thiadiazolo [2,3-a]3,3a,4,5,6,7-hexahydropyridine-3-one 1:1-dioxide (Formula I: Ar=2,6-$Cl_2$-phenyl; $R^1$=H; $R^2$ and $R^3$ together =-($CH_2$)4-) as a solid, m.p. 104.5°–106° C.

EXAMPLE 14

(a)

To a stirred solution of 7.36 ml (84.8 mmol) of chlorosulfonyl isocyanate in 180 ml of methylene chloride was added phenylmethanol (8.82 ml, 84.9 mmol) at 0° C. over a period of 35 minutes. After stirring the above solution for 2 hours at this temperature, a solution of 15.54 g (93.28 mmol) of L-proline methyl ester hydrochloride in 500 ml of methylene chloride containing triethylamine (35.5 ml) was added at 0°–5° C., and the resulting mixture was stirred overnight allowing the mixture to warm to room temperature. The reaction mixture was poured into 600 ml of 10% aq. HCl solution, saturated with sodium chloride, and the organic layer was separated. The aqueous layer was extracted with methylene chloride (2×200 ml) and the combined organic layer was washed with brine, dried and concentrated in vacuo to yield 31 g of N-(carbobenzyloxyaminosulfonyl)-L-proline methyl ester (Formula XIV: R=$CH_3$; $R^1$=H; $R^2$ and $R^3$ together =-($CH_2$)$_3$-) as an oil.

(b)

A solution of N-(carbobenzyloxyaminosulfonyl)-L-proline methyl ester (29 g) in methanol (200 ml) under nitrogen was cooled to 0° C. and 1.7 g of 10% Pd/C was added. The mixture was placed into a Parr Apparatus and hydrogenated for 2 hours at 50 psi. The catalyst was removed on a pad of CELITE® and the filtrate was concentrated in vacuo to afford, after crystallization from methanol, 10.85 g of N-(aminosulfonyl)-L-prolidine methyl ester (Formula VII: R=$CH_3$; $R^1$=H; $R^2$ and $R^3$ together =-($CH_2$)3-) as a solid.

(c)

To a solution of freshly prepared sodium methoxide (4.3 g, from 1.54 g of Na) in 150 ml of methanol was added a solution of N-(aminosulfonyl)-L-proline methyl ester (10 g; 0.067 mmol) in methanol (200 ml) and the resulting reaction mixture was heated at 70° C. for 4 hours. The mixture was cooled, neutralized with BIORAD® 50W-X8 $H^+$ ion exchange resin, and filtered. The filtrate was concentrated in vacuo to afford, after recrystallization from isopropanol, 6.0 g of tetrahydropyrrolo[1,2-b]1,2,5-thiadiazol- 3(2H)-one 1,1-dioxide (Formula IV: $R^1$=H; $R^2$ and $R^3$ together =(CH$_2$)$_3$-) as a solid.

(d)

To a mixture of tetrahydropyrrolo[1,2-b]1,2,5-thiadiazol-3(2H)-one 1,1-dioxide ( 5.0 g, 28.4 mmol) suspended in 150 ml of toluene was added phenylthiomethyl chloride (6.76 g, 42.6 mmol) and tetrabutylammonium bromide (0.91 g). The resulting mixture was refluxed for 6 hours, cooled, filtered, and the filtrate was concentrated in vacuo. The residue was purified by flash column chromatography (25%–30% ethyl acetate in hexane) to afford 5.58 g (66%) of 2-phenylthiomethyl-tetrahydropyrrolo[1,2-b]1,2,5 -thiadiazol-3 (2H)-one 1,1-dioxide (Formula VI: $R^1$=H; $R^2$ and $R^3$ together =-($CH_2$ )$_3$-) as a solid, m.p. 90.5°–91.5° C.

(e)

To a solution of 2-phenylthiomethyl-tetrahydropyrrolo[1,2-b]1,2,5-thiadiazol-3(2H)-one 1,1-dioxide (5 g) in 130 ml of methylene chloride was added sulfuryl chloride (2.02 ml) and the mixture was stirred for 2 hours at room temperature. The mixture was concentrated in vacuo, the residue triturated in hexane (2x, 150 ml, 75 ml) with stirring, the solvent decanted, and the resulting solid filtered and dried to afford 2.96 g (92%) of 2-chloromethyltetrahydropyrrolo[1,2-b]-1,2,5-thiadiazol-3(2H)-one 1,1-dioxide (Formula II: $R^1$=H; $R^2$ and $R^3$ together =-($CH_2$)$_3$-; X'=Cl) as a solid, m.p. 46.5°–47.5° C.

(f)

To a solution of $CS_2CO_3$ (0.47 g; 1.44 mmol) in 10 ml of methanol was added 0.55 g (2.88 mmol) of 2,6-dichlorobenzoic acid and the resulting mixture was stirred under nitrogen at room temperature for 3 hours. The above mixture was concentrated in vacuo to remove the excess methanol, the residue suspended in 10 ml of DMF and 2-chloromethyl-tetrahydropyrrolo[1,2-b]-1,2,5 -thiadiazol-3 (2H)-one 1,1-dioxide (0.5 g; 2.6 mmol) was added. The resulting mixture was allowed to react at 90° C. for 3 hours and then cooled. The mixture was poured into ice/water, extracted with ether/ethyl acetate (3:1; 250 ml), and the organic layer was washed with water and brine, and dried. The organic layer was concentrated in vacuo and the residue was purified by silica gel flash chromatography (35% ethyl acetate in hexane) to afford 0.6 g (61%) of 2-(2,6-dichlorophenylcarbonyloxymethyl) tetrahydropyrrolo[1,2-b]-1,2,5-thiadiazol-3(2H)-one 1,1-dioxide (Formula I: Ar=2,6-$Cl_2$-phenyl; $R^1$=H; $R^2$ and $R^3$ together =-($CH_2$)$_3$-) as a solid, m.p. 92°–93.5° C.

EXAMPLE 15

(a)

A mixture of ethyl diethoxyacetate (45 g; 255.38 mmol), glyoxylic acid (23.45 g; 246.69 mmol), and p-toluenesulfonic acid (0.347 g; 1.82 mmol) was heated at 90° C. under nitrogen for 25 hours. The mixture was cooled to −10° C. with ice/methanol bath, 24.3 g of P2O5 was added in portions, and the resulting mixture was heated to 90° C. for 2 hours. The reaction mixture was distilled in vacuo to afford 33.55 g (67%) of ethyl glyoxylate as an oil.

(b)

To a suspension of magnesium sulfate (150 g) and 1-methylphenylmethylamine (37.87 g, 32.9 mmol) in methylene chloride was added dropwise a solution of ethyl glyoxylate (33.55 g; 32.9 mmol) in methylene chloride, and the mixture was stirred at room temperature for 2 hours. The mixture was filtered, the filtrate was concentrated in vacuo to afford 67.5 g (quantitative) of N-[(1-methyl)phenylmethyl]imino-acetic acid ethyl ester, as an oil.

(c)

To a mixture of N-[(1-methyl)phenylmethyl]imino-acetic acid ethyl ester (67.5 g; 328.9 mmol) and cyclopentadiene (43.48 g, 657.8 mmol) in dry DMF under argon cooled to 0° C., was added in portions (5 ml portion) 37.5 g (328.9 mmol) of TFA followed by water (0.057 ml) and the resulting mixture was allowed to stir at room temperature for 22 hours. The above reaction mixture was poured into ice, extracted with 80% hexane in ethyl acetate (to remove excess cyclopentadiene), and the aqueous layer was slowly neutralized with sodium bicarbonate (to pH=8). The aqueous layer was extracted with ethyl acetate and the organic layer was separated and dried over sodium sulfate. The organic solvent was concentrated in vacuo to afford 52.6 g (62%) of ethyl 2-(1-phenylethyl)- 2 -azabicyclo [2,2,1 ]hept-5-en-3-carboxylate.

(d)

A solution of ethyl 2-(1-phenylethyl)-2-azabicyclo[2,2,1]hept-5-en-3-carboxylate (26.84 g; 103.9 mmol) in ethanol under nitrogen was cooled to 0° C. and 3 g of Pd(OH)$_2$ was added. The mixture was placed into a Parr Apparatus and hydrogenated for 5 hours at 60 psi. The catalyst was removed on a pad of CELITE® and the filtrate was concentrated in vacuo to afford, after crystallization from methanol, 17.58 g (quantitative) of ethyl 2 -azabicyclo[2,2,1]heptan-3-carboxylate as a solid.

(e)

To a stirred solution of 16.61 ml (191.31 mmol) of chlorosulfonyl isocyanate in methylene chloride was added phenylmethanol (19.92 ml, 191.31 mmol) at 0° C. After stirring the above solution for 2 hours at this temperature, a solution of 30.84 g (182.2 mmol) of ethyl 2-azabicyclo[2,2,1]heptan-3-carboxylate in methylene chloride containing triethylamine (42.92 ml) was added at 0° C. and the resulting mixture was stirred overnight allowing the mixture to warm to room temperature. The reaction mixture was poured into 500 ml of 10% aq. HCl solution, saturated with sodium chloride, and the organic layer was separated. The aqueous layer was extracted with methylene chloride, the combined organic layer was concentrated in vacuo and purified by flash chromatography (30% ethyl acetate in hexane) to yield 40.75 g (58.5%) of ethyl N-(carbobenzyloxyaminosulfonyl)-2-azabicyclo [2,2,1]-heptan-3-carboxylate (Formula XIV: R=Ethyl; R$^1$=H; R$^2$ and R$^3$ together =

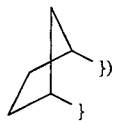

as an oil.

(f)

A solution of ethyl N-(carbobenzyloxyaminosulfonyl)-2-azabicyclo[2,2,1]heptan-3-carboxylate (40.35 g; 105.51 mmol) in methanol (300 ml) under nitrogen was cooled to 0° C. and 2.5 g of 10% Pd/C was added. The mixture was placed into a Parr Apparatus and hydrogenated for 3 hours at 50 psi. The catalyst was removed on a pad of CELITE® and the filtrate was concentrated in vacuo and purified by flash silica gel chromatography (35–40% ethyl acetate/ hexane) to afford 22.79 g (87%) of ethyl N-(aminosulfonyl)-2-azabicyclo[2,2,1]heptan-3-carboxylate (Formula VII: R=Ethyl; R$^1$=H; R$^2$ and R$^3$ together =

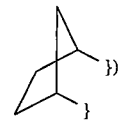

as a solid.

(g)

TO a solution of freshly prepared sodium methoxide ( from 3.34 g of Na) in 400 ml of methanol was added ethyl (N-aminosulfonyl)- 2-azabicyclo[2,2,1]heptan-3-carboxylate (20.045 g; 80.73 mmol) in one portion and the resulting reaction mixture was stirred at room temperature for 17 hours. The mixture was cooled, neutralized with BIO-RAD® 50W-X8 H$^+$ ion exchange resin (30 g), stirred for 1.5 hours, and filtered. The filtrate was concentrated in vacuo to afford 17.57 g (97.1%) of 1,2,5-thiadiazolo[2,3-b]-2-azabicyclo[2,2,1]heptan-3-one 1,1-dioxide (Formula IV: R$^1$=H; R$^2$ and R$^3$ together =

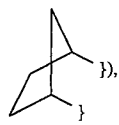

as white so a lid.

(h)

To a solution of Na salt of 1,2,5-thiadiazolo [2,3-b] -2-azabicyclo [2,2,1] -heptan-3-one 1,1-dioxide (6 g, 26.76 mmol) in acetic acid(2.5 ml) was added 4.014 g (133.8 mmol) of paraformaldehyde at room temperature. To the above mixture was added 57 ml (133.8 mmol) of HBr in acetic acid (33%) and the resulting mixture was allowed to react at 65° C. for 4 hours. The mixture was poured into 700 ml of ice/water, stirred, and the solid was filtered and dried (azeotroping with ethanol) to afford 4.79 g (69.1%) of 2-bromomethyl-1,2,5-thiadiazolo[2,3-b]-2-azabicyclo[ 2,2,1]heptan-3-one 1,1 -dioxide (Formula II: R$^1$=H; R$^2$ and R$^3$ together =

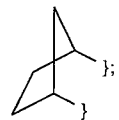

X'=Br) as as a white solid, m.p. 121°–123° C.

(i)

To a mixture of cesium salt of 2,6-dichlorobenzoic acid (prepared from 0.777 g of the acid in methanol and 663 mg of cesium carbonate, followed by removal of the solvent) in 25 ml of DMF was added 2-bromomethyl-1,2,5-thiadiazo[2,3-b]-2-azabicyclo[2,2,1]-heptan-3-one 1,1-dioxide (0.8 g; 2.71 mmol) and the mixture was allowed to stir at room temperature for 17 hours. The mixture was poured into ice/water, filtered, and the solid residue was washed with water and dried to afford 1.06 g (96.4%) of 2-2,6-dichlorophenylcarbonyloxymethyl)-1,2,5-thiadiazolo [2,3-b]-2-azabicyclo[2,2,1]heptan-3-one 1,1-dioxide (Formula I: Ar=2,6-Cl$_2$-phenyl; R$^1$=H; R$^2$ and R$^3$ together =

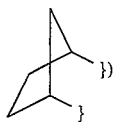

as a solid, m.p.108°–111° C.

EXAMPLE 16

(a)

To a solution of 3-bromopyridine (52.3 g; 0.33 mol) in 200 ml of glacial acetic acid was added 37.4 ml (0.33 mol) of 30% hydrogen peroxide and the mixture was refluxed for 48 hours. After adding additional peroxide ( 40 ml, 30%), the mixture was refluxed overnight. The mixture was cooled, concentrated in vacuo, the residual oil dissolved in 700 ml of ethyl acetate, and the organic layer was dried over sodium sulfate. The organic layer was concentrated in vacuo and the residue was purified by flash chromatography (ethyl acetate followed by 10% methanol in ethyl acetate) to afford 26.09 g (45%) of 3-bromopyridine N-oxide as an oil.

(b)

A mixture of 3-bromopyridine N-oxide (26.09 g; 150 mmol), trimethylsilyl cyanide (50 g; 504 mmol), and triethylamine (30.36 g, 300 mmol) in dry acetonitrile under nitrogen was refluxed for 20 hours. The mixture was concentrated in vacuo, the residue partitioned between methylene chloride (600 ml) 3 N sodium carbonate solution (250 ml), and the aqueous layer was extracted with 200 ml of methylene chloride. The combined organic layer was dried over sodium sulfate, concentrated in vacuo, and the residue was purified by flash chromatography (25% ethyl acetate in hexane) to afford 17.65 g (64.5%) of 3-bromo-2-cyano-pyridine as a solid, m.p. 93°–95° C.

(c)

To a mixture of 3-bromo-2-cyano-pyridine (13.53 g; 73.93 mmol) in 150 ml of methanol was added 25% NaOH solution (250 ml) and the resulting mixture was refluxed for 3 hours, cooled, and concentrated in vacuo. The residue was dissolved in 350 ml of methanol, cooled to 0° C. 250 ml of methanolic HCl solution was added portionwise, and the mixture was refluxed for 17 hours. The reaction mixture was cooled to 0° C. neutralized with triethylamine, concentrated in vacuo, and the residue partitioned between ethyl acetate (800 ml)/water (300 ml). The organic layer was washed with brine, dried over sodium sulfate, and concentrated in vacuo to afford 12.85 g (80.5%) of methyl 3-bromo-pyridine-2-carboxylate.

(d)

A mixture of methyl 3-bromo-pyridine-2-carboxylate (11.06 g; 51.2 mmol) Pd[PPh$_3$]$_2$Cl$_2$ (1.09 g; 1.55 mmol), and allyl-tributyltin (20.34 g; 61.44 mmol) in DMF under nitrogen was heated at 90° C. for 9.5 hours and then stirred at room temperature overnight ( 17 hours) . The mixture was poured into ice/water (450 ml) and extracted with ether (4x) . The organic layer was washed with brine, dried over sodium sulfate, and concentrated in vacuo. The resulting residue (yellow oil) was purified by flash chromatography (20%–40% ethyl acetate in hexane) to afford 10.13 g of methyl 3-allyl-pyridine-2-carboxylate as an oil, which was converted into the corresponding HCl salt, m.p. 116°–119° C.

(e)

A solution of methyl 3-allyl-pyridine-2-carboxylate hydrochloride (6.685 g, 3 9.42 mmol) in ethanol (150 ml) under nitrogen was cooled to 0° C. and 6.5 g of PtO$_2$ was added. The mixture was placed into a Parr Apparatus and hydrogenated for 24 hours at 50 psi. The catalyst was removed on a pad of CELITE® and the filtrate was concentrated in vacuo to afford, after crystallization from ethyl acetate, 7.28 g of methyl 3-propyl-piperidine-2-carboxylate hydrochloride as a solid, m.p. 130°–132° C.

(f)

To a stirred solution of 3.01 ml (34.72 mmol) of chlorosulfonyl isocyanate in 200 ml of dry methylene chloride was added phenylmethanol (3.61 ml, 34.72 mmol) at 0° C. After stirring the above solution for 1 hour at this temperature, a solution of 7.3 g (33.07 mmol) of methyl 3-propyl-piperidine-2-carboxylate hydrochloride in methylene chloride containing triethylamine (13.75 ml; 99.21 mmol) was added at 0° C., and the resulting mixture was stirred overnight (17 hours) allowing the mixture to warm to room temperature. The reaction mixture was diluted with the same volume of methylene chloride and 200 ml of 10% aq. HCl solution, saturated with sodium chloride, and the organic layer was separated. The aqueous layer was extracted with methylene chloride and the combined organic layer was washed with brine, dried and concentrated in vacuo. The residual oil was purified by flash chromatography (30% ethyl acetate in hexane) to yield 11.43 g (86.7%) of N-(carbobenzyloxyaminosulfonyl)-3-propyl-2-piperidinecarboxylic acid methyl ester(Formula XIV: R=CH$_3$; R$^1$=H; R$^2$ and R$^3$ together =-[CH(propyl)(CH$_2$)$_3$]-) as an oil.

(g)

A solution of N-(carbobenzyloxysulfonyl)-3-propyl-2-piperidine-carboxylic acid methyl ester (10.6 g; 26.6 mmol) in methanol under nitrogen was cooled to 0° C. and 1.2 g of 10% Pd/C was added. The mixture was placed into a Parr Apparatus and hydrogenated for 4 hours at 50 psi. The catalyst was removed on a pad of CELITE® and the filtrate was concentrated in vacuo and purified by flash silica gel chromatography (ethyl acetate/hexane) to afford 6.52 g (93.1%) of N-(aminosulfonyl)-3-propyl-2-piperidinecarboxylic acid methyl ester (Formula VII: R=CH$_3$; R$^1$=H; R$^2$ and R$^3$ together =-[CH(propyl)(CH$_2$)$_3$]-) as an oil.

(h)

To a solution of freshly prepared sodium methoxide ( from 5 0.958 g of Na; 41.69 mmol) in methanol was added N-(aminosulfonyl)- 3-propyl-2-piperidinecarboxylic acid methyl ester (6.1 g; 23.16 mmol) in one portion and the resulting reaction mixture was stirred at room temperature for 17 hours. The mixture was cooled, concentrated in vacuo, the residue was partitioned between 1 N HCl solution (50 ml) and ethyl acetate, and the aqueous layer was extracted with ethyl acetate (2x). The combined organic layer was dried over sodium sulfate and concentrated in vacuo to afford 5.38 g (theory) of 4-propyl-1,2,5-thiadiazolo [2,3-a]3,3a, 4,5,6,7 -hexahydropyridine-3-one 1,1-dioxide (Formula IV: $R^1$=H; $R^2$ and $R^3$ together =-[CH(propyl)($CH_2$)$_3$]-).

(i)

To a solution of 4-propyl-1,2,5-thiadiazolo [2,3-a]3,3a,4, 5,6,7-hexahydropyridine-3-one 1,1-dioxide (0.5 g, 2.15 mmol) suspended in 15 ml of glacial acetic acid was added paraformaldehyde (0.323 g; 10.75 mmol) followed by HBr/ acetic acid (1.52 g, 33%) solution and the resulting mixture was heated at 80° C. for 6 hours, cooled, and poured into ice/water. The mixture was extracted with methylene chloride (3x), the organic layer was washed with saturated sodium bicarbonate solution and dried over sodium sulfate. The organic solvent was concentrated in vacuo to afford 0.604 g (86.4%) of 2-bromomethyl-4-propyl-1,2,5-thiadiazolo [2,3-a]3,3a,4,5,6,7-hexahydropyridine-3-one 1,1-dioxide (Formula II: $R^1$=H; $R^2$ and $R^3$ together =-[CH(propyl)($CH_2$)$_3$ ]-; X'=Br) as an oil.

(j)

To a mixture of cesium salt of 2,6-dichlorobenzoic acid (from 0.441 g of acid in methanol with 378 mg of cesium carbonate) in DMF was added 2-bromomethyl-4-propyl-1, 2,5-thiadiazolo- [2,3-a]3,3a,4,5,6,7-hexahydropyridine-3-one 1,1-dioxide (0.5 g; 1.54 mmol), and the mixture was allowed to stir under nitrogen and at room temperature for 17 hours. The mixture was poured into 150 ml of ice/water, extracted with ethyl acetate (3x), the organic layer was washed with brine and dried over sodium sulfate. The solvent was concentrated in vacuo and the residue was purified by silica gel chromatography to afford, after crystallization from ether/hexane, 0.586 g (87.5%) of 2-(2,6-dichlorophenylcarbonyloxymethyl)- 4-propyl-1,2,5-thiadiazolo [2,3-a]3,3a, 4,5,6,7-hexahydropyridine-3-one 1,1-dioxide (Formula I: At=2, 6-$Cl_2$-phenyl; $R^1$=H; $R^2$ and $R^3$ together =-[CH(propyl)($CH_2$)$_3$]-) as a solid, m.p.102°–103° C.

Following a procedure similar to that described in Example 10 (b), but substituting an appropriate cesium salt of a compound of the Formula III for the cesium salt of 2, 6-dichloro-3-[2-(4morpholino) ethoxy]benzoic acid and, if applicable, a suitable compound of the Formula II for 2-chloromethyl-4-(3-methylbutyl)-5 -methyl-1,2,5-thiadiazolidin-3-one 1,1-dioxide, it is contemplated that there can be prepared the following compounds of the Formula I illustrated in Table I.

TABLE I

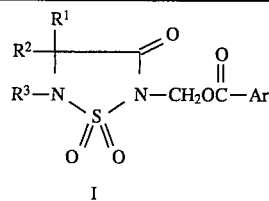

I

| Example No. | Ar | $R^1$ | $R^2$ | $R^3$ |
|---|---|---|---|---|
| 17 | 2,6-($CH_3$)$_2$-Phenyl | H | propyl | H |
| 18 | 2,6-($CF_3$)$_2$-phenyl | H | isopropyl | H |
| 19 | 2,4($CH_3$O)$_2$-phenyl | H | propyl | $CH_3$ |
| 20 | 2,6-$Cl_2$-3-[O($CH_2$)$_2$N($CH_3$)$_2$] phenyl | H | isopropyl | propyl |
| 21 | 2,6-$Cl_2$-3-[O($CH_2$)$_2$-1-piperidinyl] phenyl | H | propyl | ethyl |
| 22 | 2,6-$Cl_2$-3-[O($CH_2$)$_2$-1-azetidinyl] phenyl | propyl | $CH_3$ | $CH_3$ |
| 23 | 2,6-$Cl_2$-4-[O($CH_2$)$_2$-1-piperazinyl] phenyl | H | ($CH_2$)$_2$CH($CH_3$)$_2$ | $CH_3$ |
| 24 | 2,6-$Cl_2$-4-[O($CH_2$)$_2$-1-imidazolyl] phenyl | H | $CH_2$Ph | $CH_3$ |

Biological Test Results

Representative examples of the compounds of the invention have been found to possess valuable pharmacological properties. In particular, they have been found to inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

The pharmacological properties of representative examples of the compounds of the invention were demonstrated by the following conventional in vitro biological test procedure.

The test compound (inhibitor) is dissolved in DMSO in a vial to produce an inhibitor stock solution which has a concentration in the range of 200–1000 μM. The inhibitor stock solution is diluted (1:4, 1:16 and 1:64) into assay vials (vials 1, 2 and 3 respectively) containing 2.4 mL of buffer solution (50 mM N- [2-hydroxyethyl ] piperazine-N'-[2-ethanesulfonic acid]/NaOH, 500 mM NaCl, pH 7.8 at 25° C.) and DMSO is added so that the total volume in each vial is 3.2 mL. 70 μL, 50 μL, 35 μL and 25 μL of inhibitor from assay vial 1 is placed into the first four wells of a 96-well microtiter plate and each well is made up to 90 μL total volume with the addition of a 25% DMSO/buffer solution. The inhibitor from assay vials 2 and 3 is processed in a similar manner and placed in wells 5–12 respectively to afford a total of 12 different inhibitor concentrations. Four wells (wells 13–16) containing 90 μL of the 25% DMSO/ buffer solution but no inhibitor are also run simultaneously with the inhibited wells as a control. 150 μL of substrate solution (prepared by the addition of 500 μL of the human leukocyte elastase (HLE) substrate MeOSuc-Ala-Ala-Pro-Val-pNA (18.7 mM in DMSO) to 19.5 mL of buffer solution) is then added simultaneously into each of the 16 wells and the solution in each well was thoroughly mixed.

The 96-well microtiter plate is placed into a Microplate Reader #89815A spectrophotometer and 110 μL of the enzyme solution (prepared as follows: a mixture of 20 mL of buffer solution and 20 mg of bovine serum albumen is gently vortexed in a scintillation vial and 5 μL HLE stock solution (1 mg/mL dissolved in deionized water) is added) is added simultaneously to each of the 16 wells. Each of the solutions in the wells is throughly mixed and then the time-dependent absorbance data is collected at an absorbance of 410 nM until the assay is complete. It should be noted that although this assay method can be done manually, it is preferred to perform the assay robotically using a Hewlett Packard MicroAssay System Robot.

A plot of the absorbance versus time data thus obtained affords progress curves the final slope of which is equal to the final steady-state velocities (VF). Using the program ENZFITTER (Elsevier software), the progress curves for the four control assays ([I]=0) are fit by linear regression to yield the enzyme reaction velocity values in the absences of inhibitor ($V_o$) which are averaged to produce a single fixed value. The inhibition constant $K_i$(nM) is then obtained from a plot of $$\frac{[I]}{1 - V_F/V_o} \text{ versus } V_o V_F$$

which affords a linear plot wherein $$\text{slope} = K_i \left( 1 + \frac{[S]}{Km} \right)$$

and [S] is the concentration of the substrate and $K_m$ is the Michaelis constant.

Table II summarizes the results obtained from the testing of representative compounds of the invention for human leukocyte elastase inhibitory activity.

TABLE II

| Example No. | $K_i$ (nM) |
|---|---|
| 1(f) | 12 |
| 2(f) | 350 |
| 3(i) | 0.11 |
| 4(f) | 25 |
| 5(e) | 0.5 |
| 6(k) | 120 |
| 7(h) | 4.4 |
| 8(i) | 0.06 |
| 9(c) | 0.26 |
| 10(b) | 0.20 |
| 11(g) | 0.62 |
| 12 | 0.45 |
| 13(f) | 22 |
| 14(f) | 170 |
| 15(i) | 3700 |
| 16(j) | 9.6 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

I claim:

1. A compound of the formula:

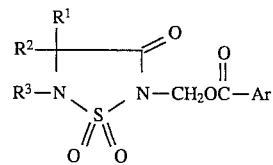

wherein:

Ar is phenyl, or phenyl substituted with from one to three, the same or different, members of the group consisting of lower-alkyl, perfluorolower-alkyl, perchlorolower-alkyl, lower-alkoxy, halogen, hydroxy, and -O-(alkylene)-N=B, wherein N=B is amino, lower-alkylamino, dilower-alkylamino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, or 1-imidazolyl;

$R^1$ is hydrogen, lower-alkyl, phenyl-lower-alkyl, or halolower-alkyl;

$R^2$ is hydrogen, lower-alkyl, phenyl-lower-alkyl, or halolower-alkyl; and $R^3$ is hydrogen, or lower-alkyl; or $R^2$ and $R^3$ together are

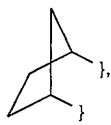

1,3-propylene, 1,4-butylene, or either of 1,3-propylene or 1,4-butylene substituted with one or two lower-alkyl groups; v or pharmaceutically acceptable acid-addition salts of basic members thereof; or where applicable, an enantiomer or a racemic mixture thereof.

2. A compound according to claim 1 wherein Ar is phenyl, or phenyl substituted with from one to three, the same or different, members of the group consisting of lower-alkyl, lower-alkoxy, halogen, hydroxy, and -O-(alkylene)-N=B, wherein N=B is 1-pyrrolidinyl or 4-morpholinyl.

3. A compound according to claim 2 wherein Ar is phenyl substituted with from one to three, the same or different, members of the group consisting of halogen, and -O-(alkylene)-N=B.

4. A compound according to claim 3 wherein $R^1$ is hydrogen, methyl, propyl, isopropyl, $(CH_2)_2C (Cl) (CH_3)_2$, 3-methylbutyl, or benzyl; $R^2$ is hydrogen, methyl, propyl, isopropyl, $(CH_2)_2C (Cl) (CH_3)$ 2,3-methylbutyl, or benzyl; and $R^3$ is hydrogen, methyl, or ethyl; or $R^2$ and $R^3$ together ar

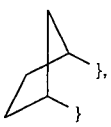

1,3-propylene, 1,4-butylene, or either of 1,3-propylene or 1,4-butylene substituted with one or two lower-alkyl groups.

5. A compound according to claim 4 wherein Ar is phenyl substituted by from one to three, the same or different, members of the group consisting of chlorine, -O-$(CH_2)_2$-1-pyrrolidinyl, and -O-$(CH_2)_2$-4-morpholinyl.

6. A compound according to claim 5 selected from the group consisting of:

2-(2,6-dichlorophenylcarbonyloxymethyl)-4-propyl-5-methyl- 1,2,5-thiadiazolidin-3-one 1,1-dioxide; and 2-(2,6-dichlorophenylcarbonyloxymethyl)-4-(3-methylbutyl)- 5-methyl-1,2,5-thiadiazolidin-3-one 1,1-dioxide.

7. A pharmaceutical composition for the treatment of degenerative diseases which comprises a pharmaceutically acceptable carrier, adjuvant, diluent or vehicle together with an effective serine proteases inhibiting amount of a compound according to claim 1.

8. A pharmaceutical composition for the treatment of degenerative diseases which comprises a pharmaceutically acceptable carrier, adjuvant, diluent or vehicle together with an effective serine proteases inhibiting amount of a compound according to claim 2.

9. A pharmaceutical composition for the treatment of degenerative diseases which comprises a pharmaceutically acceptable carrier, adjuvant, diluent or vehicle together with an effective serine proteases inhibiting amount of a compound according to claim 3.

10. A pharmaceutical composition for the treatment of degenerative diseases which comprises a pharmaceutically acceptable carder, adjuvant, diluent or vehicle together with an effective serine proteases inhibiting amount of a compound according to claim 4.

11. A pharmaceutical composition for the treatment of degenerative diseases which comprises a pharmaceutically acceptable carder, adjuvant, diluent or vehicle together with an effective serine proteases inhibiting amount of a compound according to claim 5.

12. A pharmaceutical composition for the treatment of degenerative diseases which comprises a pharmaceutically acceptable carrier, adjuvant, diluent or vehicle together with an effective serine proteases inhibiting amount of a compound according to claim 6.

13. A method for the treatment of degenerative diseases which comprises administering to a patient in need of such treatment an effective serine proteases inhibiting amount of a compound according to claim 1.

14. A method for the treatment of degenerative diseases which comprises administering to a patient in need of such treatment an effective serine proteases inhibiting amount of a compound according to claim 2.

15. A method for the treatment of degenerative diseases which comprises administering to a patient in need of such treatment an effective serine proteases inhibiting amount of a compound according to claim 3.

16. A method for the treatment of degenerative diseases which comprises administering to a patient in need of such treatment an effective serine proteases inhibiting amount of a compound according to claim 4.

17. A method for the treatment of degenerative diseases which comprises administering to a patient in need of such treatment an effective serine proteases inhibiting amount of a compound according to claim 5.

18. A method for the treatment of degenerative diseases which comprises administering to a patient in need of such treatment an effective serine proteases inhibiting amount of a compound according to claim 6.

19. A method according to claim 13 wherein said degenerative diseases are selected from emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

20. A method according to claim 19 wherein said degenerative diseases are selected from emphysema, cystic fibrosis, chronic bronchitis, and adult respiratory distress syndrome.

\* \* \* \* \*